United States Patent
Telfort

(10) Patent No.: US 9,750,461 B1
(45) Date of Patent: Sep. 5, 2017

(54) ACOUSTIC RESPIRATORY MONITORING SENSOR WITH PROBE-OFF DETECTION

(71) Applicant: Masimo Corporation, Irvine, CA (US)

(72) Inventor: Valery G. Telfort, Laval (CA)

(73) Assignee: Masimo Corporation, Irvine, CA (US)

( * ) Notice: Subject to any disclaimer, the term of this patent is extended or adjusted under 35 U.S.C. 154(b) by 307 days.

(21) Appl. No.: 14/137,629

(22) Filed: Dec. 20, 2013

Related U.S. Application Data

(60) Provisional application No. 61/748,381, filed on Jan. 2, 2013.

(51) Int. Cl.
| | |
|---|---|
| A61B 5/00 | (2006.01) |
| A61B 7/00 | (2006.01) |
| A61B 5/0205 | (2006.01) |
| A61B 5/026 | (2006.01) |
| A61B 5/0295 | (2006.01) |
| A61B 5/0402 | (2006.01) |
| A61B 7/02 | (2006.01) |
| A61B 7/04 | (2006.01) |

(52) U.S. Cl.
CPC .......... *A61B 5/7221* (2013.01); *A61B 5/0205* (2013.01); *A61B 5/0261* (2013.01); *A61B 5/0295* (2013.01); *A61B 5/0402* (2013.01); *A61B 5/725* (2013.01); *A61B 5/726* (2013.01); *A61B 5/7246* (2013.01); *A61B 5/7257* (2013.01); *A61B 5/7278* (2013.01); *A61B 7/026* (2013.01); *A61B 7/04* (2013.01)

(58) Field of Classification Search
CPC ...... A61B 7/026; A61B 5/7217; A61B 5/7257
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |

(Continued)

FOREIGN PATENT DOCUMENTS

| | | | | |
|---|---|---|---|---|
| IL | EP 0956820 A1 | * | 11/1999 | ............. A61B 5/087 |

OTHER PUBLICATIONS

US 8,845,543, 09/2014, Diab et al. (withdrawn)

*Primary Examiner* — Gary Jackson
*Assistant Examiner* — Amanda Steinberg
(74) *Attorney, Agent, or Firm* — Knobbe Martens Olson & Bear, LLP

(57) ABSTRACT

Embodiments described herein include sensors and sensor systems having probe-off detection features. For example, sensors and physiological monitors described herein include hardware and/or software capable of providing an indication of the integrity of the connection between the sensor and the patient. In various embodiments, the physiological monitor is configured to output an indication of a probe-off condition for an acoustic sensor (or other type of sensor). For example, in an embodiment, a signal from an acoustic sensor is compared with a signal from a second sensor to determine a probe-off condition.

8 Claims, 23 Drawing Sheets

(56) References Cited

U.S. PATENT DOCUMENTS

| | | |
|---|---|---|
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A * | 7/1996 | Kaspari ............ A61B 5/02007 128/925 |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,290,654 B1 * | 9/2001 | Karakasoglu ........ A61B 5/087 128/201.23 |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 * | 2/2003 | Kiani .................. A61B 5/6843 600/322 |
| 6,527,729 B1 * | 3/2003 | Turcott ................ A61B 5/0002 600/528 |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |

(56) References Cited

U.S. PATENT DOCUMENTS

| | | |
|---|---|---|
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |

(56) References Cited

U.S. PATENT DOCUMENTS

| | | |
|---|---|---|
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |

(56) References Cited

U.S. PATENT DOCUMENTS

| | | |
|---|---|---|
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 2007/0055151 A1* | 3/2007 | Shertukde .......... A61B 5/02007 600/437 |
| 2007/0263208 A1* | 11/2007 | Yelin .................. A61B 5/0066 356/307 |
| 2009/0240467 A1* | 9/2009 | Anbari ............... G05B 23/0221 702/179 |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0319724 A1* | 12/2011 | Cox ................... A61B 5/02028 600/301 |
| 2012/0059267 A1 | 3/2012 | Lamego et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0303520 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |

(56) References Cited

U.S. PATENT DOCUMENTS

| | | |
|---|---|---|
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |

\* cited by examiner

ACOUSTIC RESPIRATORY MONITORING SENSOR WITH PROBE-OFF DETECTION

RELATED APPLICATIONS

This application is a nonprovisional of U.S. Provisional Application No. 61/748,381, filed Jan. 2, 2013, titled "Acoustic Respiratory Monitoring Sensor With Probe-Off Detection", the disclosure of which is hereby incorporated by reference in its entirety.

BACKGROUND

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

SUMMARY

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught or suggested herein without necessarily achieving others.

Embodiments described herein include sensors and sensor systems having probe-off detection features. For example, sensors and physiological monitors described herein include hardware and/or software capable of providing an indication of the integrity of the connection between the sensor and the patient. In various embodiments, the physiological monitor is configured to output an indication of a probe-off condition for an acoustic sensor (or other type of sensor). For example, in an embodiment, a signal from an acoustic sensor is compared with a signal from a second sensor to determine a probe-off condition.

In certain embodiments, a method of determining a connection state between a non-invasive acoustic sensor and a medical patient can include receiving an acoustic physiological signal from an acoustic sensor coupled with a medical patient. Further, the method can include receiving a second physiological signal from a second sensor coupled with the medical patient. Moreover, the method can include comparing, with one or more processors, the acoustic physiological signal and the second physiological signal. In some embodiments, in response to said comparison, the method can include outputting an indication of whether one or both of the non-invasive acoustic sensor and the second sensor is properly connected to the patient.

Additionally, in certain embodiments, a system for determining a connection state between a non-invasive acoustic sensor and a medical patient can include one or more processors that can receive an acoustic physiological signal from an acoustic sensor coupled with a medical patient. The system can further receive a second physiological signal from a second sensor coupled with the medical patient. Moreover, the system can determine, with one or more processors, whether the acoustic physiological signal is at least partially correlated with the second physiological signal. Additionally, in response to a determination that the acoustic physiological signal is at least partially correlated with the second physiological signal, the system can output an indication of whether one or both of the non-invasive acoustic sensor and the second sensor is properly connected to the patient.

Furthermore, in some embodiments, a method of determining a connection state between a non-invasive acoustic sensor and a medical patient can include receiving an acoustic physiological signal from an acoustic sensor, the acoustic physiological signal reflecting first physiological information of a patient. Further, the method can include receiving a photoplethysmograph signal from an optical sensor, the photoplethysmograph signal reflecting second physiological information of the patient. The method can also include comparing, with one or more processors, the acoustic physiological signal and the photoplethysmograph signal. Moreover, in response to said comparing, the method can further include outputting an indication of whether the acoustic sensor is properly connected to the patient.

In certain embodiments, a method of determining a connection state between a non-invasive acoustic sensor and a medical patient, the method can include receiving an acoustic physiological signal from an acoustic sensor coupled with a medical patient. Further, the method can include analyzing low frequency content of the acoustic physiological signal with one or more processors. The method can also, in response to said analysis of the low frequency content, include outputting an indication of whether the acoustic sensor is properly connected to the patient. In some embodiments, the method can further include receiving a second acoustic physiological signal from a second acoustic sensor positioned over a chest of the medical patient. Furthermore, the method can include identifying a second heart sound feature in the second acoustic waveform where in some embodiments said analyzing the low frequency content of the acoustic physiological signal includes identifying a feature of the acoustic physiological signal that corresponds to the second heart sound feature in the second acoustic waveform.

Moreover, in some embodiments, a method of determining a connection state between a non-invasive acoustic sensor and a medical patient, can include receiving an acoustic physiological signal from an acoustic sensor coupled with a medical patient. The method can further include extracting a low frequency waveform from the acoustic physiological signal. In addition, the method can include comparing the low frequency waveform with a database of pulse rate waveforms with one or more processors. The method can include in response to determining that the low frequency waveform does not have a substantial match in the database of pulse rate waveforms, outputting a probe-off indication.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

DETAILED DESCRIPTION

Figure 1A:
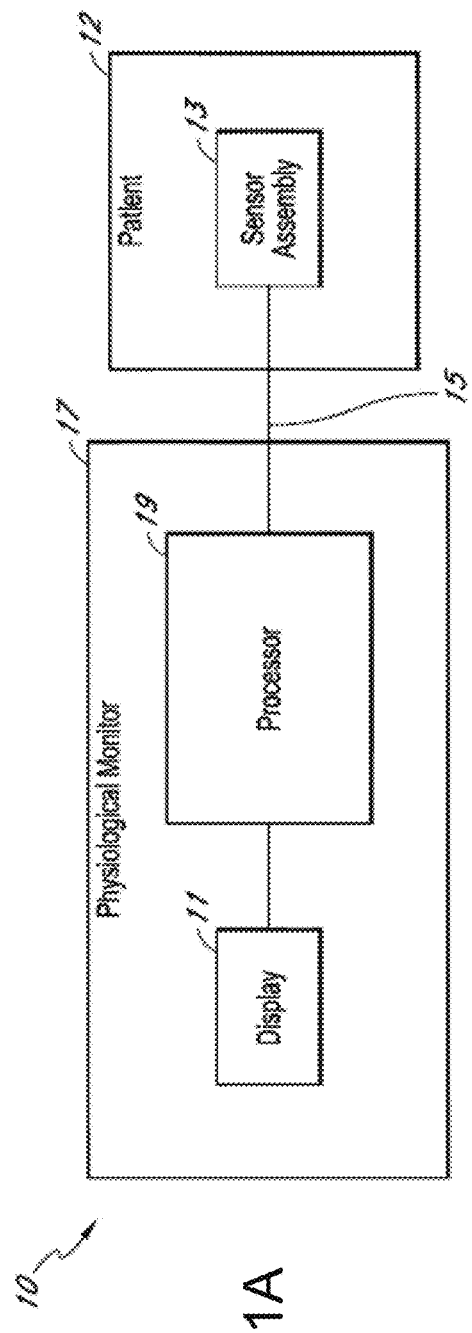
FIGS. 1A-B are block diagrams illustrating physiological monitoring systems in accordance with embodiments of the disclosure.

Various embodiments will be described hereinafter with reference to the accompanying drawings. These embodiments are illustrated and described by example only, and are not intended to be limiting.

I. Introduction

Certain existing patient monitoring systems include biological sound sensors that capture patient bodily sounds (e.g., heart sounds, breathing, digestive system sounds, vocalization and other speech sounds, etc.) and physiological monitors which process the captured sounds to determine physiological parameters. Such systems generally rely on a robust connection between the sensor and the patient to reliably detect and process the targeted bodily sounds. As such, a probe-off condition, such as (for example) a faulty or unstable connection between the sensor (e.g., the probe) and the patient, can lead to a number of problems, particularly where the patient monitor or medical personnel are not made aware of the issue.

When the physiological monitor is not aware of a faulty connection between the sensor and patient, the monitor may misinterpret readings detected by the sensor. For example, the monitor may indicate false alarm conditions. In one instance, where the system is configured to detect patient breathing sounds and determine a corresponding respiratory rate, the monitor may falsely determine that the patient is not breathing, instead of merely indicating that the sensor has detached from the patient's skin. The system may additionally detect significant amounts of environmental noise due to a probe-off condition, and then improperly present the detected noise as physiological signal. Moreover, medical personnel may similarly misinterpret results presented by the monitor when the personnel are not aware of a faulty connection, possibly leading to misdiagnoses or other issues.

Embodiments described herein include sensors and sensor systems having probe-off detection features. For example, sensors and physiological monitors described herein include hardware and/or software capable of providing an indication of the integrity of the connection between the sensor and the patient. In various embodiments, the physiological monitor is configured to output an indication of a probe-off condition for an acoustic sensor (or other type of sensor). For example, in an embodiment, a signal from an acoustic sensor is compared with a signal from a second sensor to determine a probe-off condition. The second sensor may be an optical sensor, electroencephalography (EEG) sensor, electrocardiograph (ECG) sensor, a second acoustic sensor, combinations of the same, or another type of sensor. In one embodiment, the pulse rate of a patient can be independently measured with both the acoustic sensor and the second sensor. A lack of correlation between pulse rate measured by both sensors may indicate a probe-off condition for either the acoustic sensor or the second sensor. Other techniques for determining probe-off conditions are described in greater detail below, including embodiments where a single acoustic sensor is used to determine a probe-off condition.

The probe-off techniques described herein can be used in a variety of ways to improve patient monitoring. For example, the patient monitor can provide medical personnel with an indication of the quality of the attachment state of the sensor, such as "sensor connected," "sensor disconnected," "sensor improperly connected," an indication (e.g., a percentage or other alphanumeric indication) as to the degree of the connection quality, or some other indication of the connection quality, combinations of the same, or the like.

Additionally, the sensor, monitor, and/or user may use the indication of the attachment state to avoid false positive (e.g., alarm) conditions. For example, where a system is monitoring patient breathing sounds and the sensor becomes disconnected, the monitor can use the probe-off functionality to avoid reporting a false alarm to medical personnel that the patient is not breathing. Instead, the monitor can report the probe-off and/or false alarm condition to personnel, who can in turn fix the faulty connection. A wide variety of other uses or combinations of the uses described herein are possible. For example, in one embodiment, the sensor or monitor stops detecting and/or reporting sound information when the sensor is not properly attached to a patient. Moreover, by alerting medical personnel to probe-off conditions, the probe-off module reduces the risk that the probe-off condition and therefore physiological sounds of interest will go un-monitored for extended periods of time.

While described with respect to acoustic sensors configured to detect physiological sounds of a patient, many of the techniques described herein are compatible with other types of patient sensors (e.g., pulse oximetry sensors, capnography sensors, ECG sensors, EEG sensors, bioimpedance sensors, blood pressure sensors, and the like).

II. Example Acoustic System Overview

Prior to describing probe-off features in detail, an overview of example acoustic monitoring sensors and systems is provided below with respect to FIGS. 1A-1C. Example embodiments describing probe-off functionality are described below with respect to FIGS. 2-13.

In various embodiments, an acoustic monitoring system includes an acoustic signal processing system that measures and/or determines any of a variety of physiological parameters of a medical patient. For example, in an embodiment, the physiological monitoring system includes an acoustic monitor. The acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate to help with probe off detection, heart sounds (S1, S2, S3, S4, and murmurs), and change in heart sounds such as normal to murmur or split heart sounds indicating fluid overload. Moreover, the acoustic signal processing system may (1) use a second probe over the chest for additional heart sound detection; (2) keep the user inputs to a minimum (example, height); and/or (3) use a Health Level 7 (HL7) interface to automatically input patient demography.

In certain embodiments, the physiological monitoring system includes an electrocardiograph (ECG or EKG) system that measures and/or determines electrical signals generated by the cardiac system of a patient. The ECG system can include one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, an optical photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt, a bioimpedance sensor for measuring respiratory effort, an EEG sensor for measuring brain activity, and the like. In certain embodiments, these sensors are combined in a single processing system which processes signal output from the sensors on a single multi-function circuit board or multiple circuit boards.

Figure 1B:
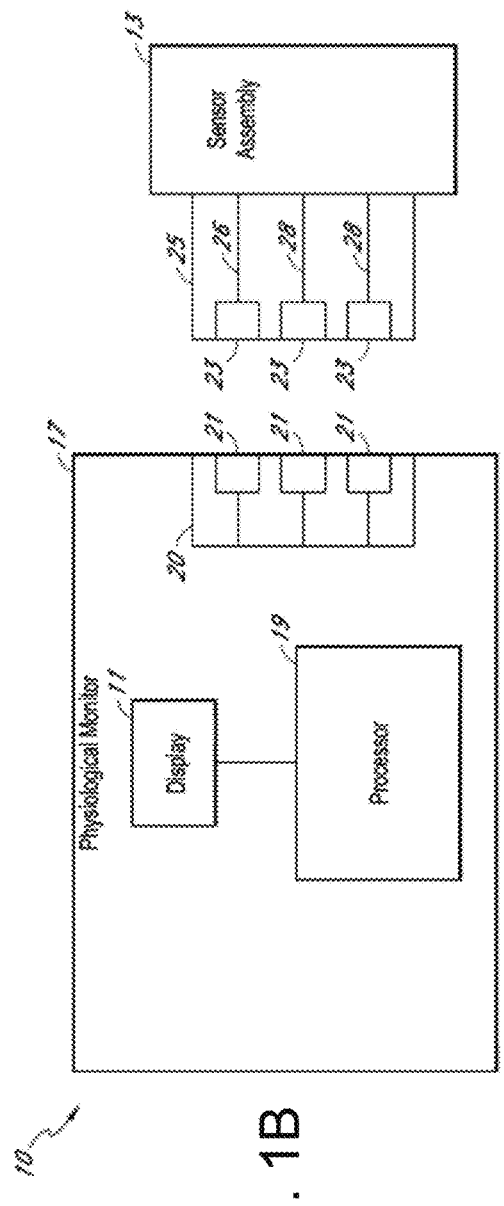
Figure 2:
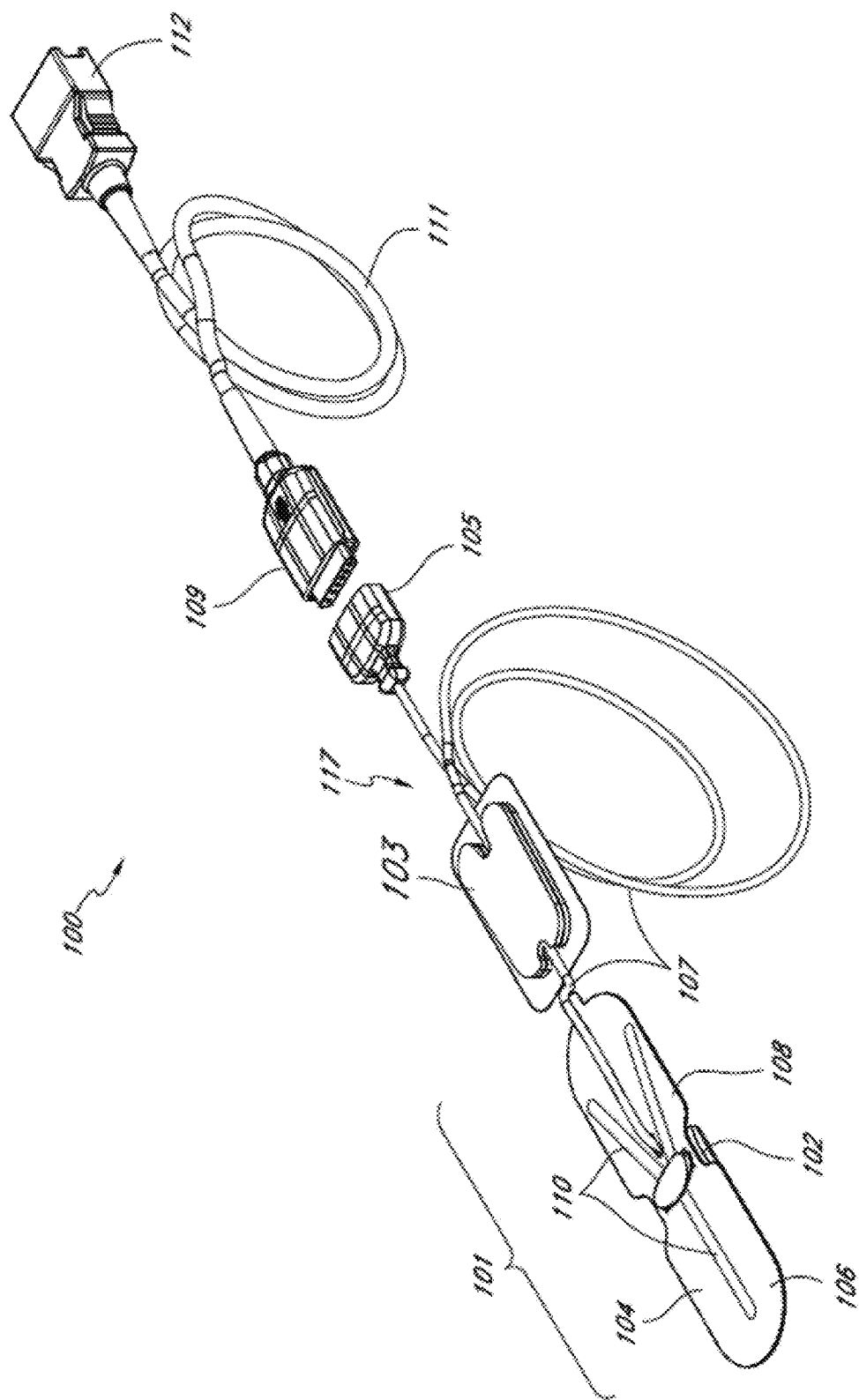
FIG. 2 is a top perspective view illustrating portions of a sensor system in accordance with an embodiment of the disclosure.

Referring specifically to the drawings, FIGS. 1A, 1B, and 2 illustrate example patient monitoring systems, sensors, and cables that can be used to provide acoustic physiological monitoring of a patient, such as respiratory monitoring, with probe-off detection.

For example, FIG. 1A shows an embodiment of a physiological monitoring system 10. In the physiological monitoring system 10, a medical patient 12 is monitored using one or more sensors 13, each of which transmits a signal over a cable 15 or other communication link or medium to a physiological monitor 17. The physiological monitor 17 includes a processor 19 and, optionally, a display 11. The one or more sensors 13 include sensing elements such as, for example, acoustic piezoelectric devices, electrical ECG leads, pulse oximetry sensors, or the like. The sensors 13 can generate respective signals by measuring a physiological parameter of the patient 12. The signals are then processed by one or more processors 19. The one or more processors 19 then communicate the processed signal to the display 11 if a display 11 is provided. In an embodiment, the display 11 is incorporated in the physiological monitor 17. In another embodiment, the display 11 is separate from the physiological monitor 17. The monitoring system 10 is a portable monitoring system in one configuration. In another instance, the monitoring system 10 is a pod, without a display, and is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two acoustic sensors. In still another embodiment, the one or more sensors 13 include at least two acoustic sensors and one or more ECG sensors, pulse oximetry sensors, bioimpedance sensors, capnography sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the acoustic sensor 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors, one or more additional cables 115 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

FIG. 2 an embodiment of a sensor system 100 including a sensor 101 suitable for use with any of the physiological monitors shown in FIGS. 1A and 1B. The sensor system 100 includes a sensor 101, a sensor cable 117, a patient anchor 103 attached to the sensor cable 117, and a connector 105 attached to the sensor cable 117. The sensor 101 includes a shell 102 configured to house certain componentry of the sensor 101, and an attachment subassembly 104 positioned the sensor 101 and configured to attach the sensor 101 to the patient.

The sensor 101 can be removably attached to an instrument cable 111 via an instrument cable connector 109. The instrument cable 111 can be attached to a cable hub 120, which includes a port 121 for receiving a connector 112 of the instrument cable 111 and a second port 123 for receiving another cable. In certain embodiments, the second port 123 can receive a cable connected to a pulse oximetry or other sensor. In addition, the cable hub 120 could include additional ports in other embodiments for receiving additional cables. The hub includes a cable 122 which terminates in a connector 124 adapted to connect to a physiological monitor (not shown). In another embodiment, no hub is provided and the acoustic sensor 101 is connected directly to the monitor, via an instrument cable 111 or directly by the sensor cable 117, for example. Examples of compatible hubs are described in U.S. patent application Ser. No. 12/904,775, which is incorporated by reference in its entirety herein. Examples of acoustic sensors are described in U.S. Patent Application No. 61/703,731, which is incorporated by reference in its entirety herein.

The component or group of components between the sensor 101 and the monitor in any particular embodiment may be referred to generally as a cabling apparatus. For example, where one or more of the following components are included, such components or combinations thereof may be referred to as a cabling apparatus: the sensor cable 117, the connector 105, the cable connector 109, the instrument cable 111, the hub 120, the cable 122, and/or the connector 124. It should be noted that one or more of these components may not be included, and that one or more other components may be included between the sensor 101 and the monitor, forming the cabling apparatus.

In an embodiment, the acoustic sensor 101 includes one or more sensing elements (not shown), such as, for example, a piezoelectric device or other acoustic sensing device. Where a piezoelectric membrane is used, a thin layer of conductive metal can be deposited on each side of the film as electrode coatings, forming electrical poles. The opposing surfaces or poles may be referred to as an anode and cathode, respectively. Each sensing element can be configured to mechanically deform in response to sounds emanating from the patient (or other signal source) and generate a corresponding voltage potential across the electrical poles of the sensing element.

The shell 102 according to certain embodiments houses a frame (not shown) or other support structure configured to support various components of the sensor 101. The one or more sensing elements can be generally wrapped in tension around the frame. For example, the sensing elements can be positioned across an acoustic cavity disposed on the bottom surface of the frame. Thus, the sensing elements according to some embodiments are free to respond to acoustic waves incident upon them, resulting in corresponding induced voltages across the poles of the sensing elements.

Additionally, the shell 102 can include an acoustic coupler not shown), which advantageously improves the coupling between the source of the signal to be measured by the sensor (e.g., the patient's body) and the sensing element. The acoustic coupler 102 of one embodiment includes a bump positioned to apply pressure to the sensing element so as to bias the sensing element in tension. For example, the bump can be positioned against the portion of the sensing element that is stretched across the cavity of the frame. In one embodiment, the acoustic coupler further includes a protrusion (not shown) on the upper portion of the inner lining, which exerts pressure on the backbone 110 (discussed below) and other internal components of the sensor 101.

The attachment portion 107 helps secure the sensor assembly 101 to the patient. The illustrated attachment portion 107 includes first and second attachment arms 106, 108. The attachment arms can be made of any number of materials, such as plastic, metal or fiber. Furthermore, the attachment arms can be integrated with the backbone (discussed below). The underside of the attachment arms 106, 108 include patient adhesive (e.g., in some embodiments, tape, glue, a suction device, etc.), which can be used to secure the sensor 101 to a patient's skin. The example attachment portion 107 further includes a resilient backbone member 110 which extends into and forms a portion of the attachment arms 106, 108. The backbone 110 can be placed above or below the attachment arms 106, 108, or can be placed between an upper portion and a lower portion of the attachment arms 106, 108. Furthermore, the backbone can be constructed of any number of resilient materials, such as plastic, metal, fiber, combinations thereof, or the like.

As the attachment arms 106, 108 are brought down into contact with the patient's skin on either side of the sensor 102, the adhesive affixes to the patient. Moreover, the resiliency of the backbone 110 causes the sensor 101 to be beneficially biased in tension against the patient's skin and/or reduces stress on the connection between the patient adhesive and the skin. Further examples of compatible attachment portions, associated functionality and advantages are described in U.S. application Ser. No. 12/643,939 (the '939 Application) previously incorporated by reference. For example, embodiments of attachment portions are shown in and described with respect to FIGS. 2B, 2C, 9A-9D and 10 of the '939 Application, and are explicitly incorporated by reference herein.

Moreover, as will be described in greater detail, the attachment portion 107 can also advantageously work together with other sensor componentry to provide an indication to the monitor or to the user as to the attachment state of the sensor.

The acoustic sensor 101 can further include circuitry for detecting and transmitting information related to biological sounds to the physiological monitor. These biological sounds can include heart, breathing, and/or digestive system sounds, in addition to many other physiological phenomena. The acoustic sensor 101 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein (the '883 Application). In other embodiments, the acoustic sensor 101 is a biological sound sensor such as those described in U.S. Pat. No. 6,661,161 or U.S. patent application Ser. No. 12/643, 939, filed on Dec. 21, 2009 (the '939 Application), both of which are incorporated by reference herein in their entirety. Other embodiments include other suitable acoustic sensors. For example, in certain embodiments, compatible acoustic sensors can be configured to provide a variety of auscultation functions, including live and/or recorded audio output (e.g., continuous audio output) for listening to patient bodily or speech sounds. Examples of such sensors and sensors capable of providing other compatible functionality can be found in U.S. patent application Ser. No. 12/905,036 entitled PHYSIOLOGICAL ACOUSTIC MONITORING SYSTEM, filed on Oct. 14, 2010, previously incorporated by reference herein in its entirety.

While an example sensor system 100 has been provided, embodiments described herein are compatible with a variety of sensors and associated components.

III. Example Systems and Sensors Incorporating Probe-Off Functionality

Figure 3A:
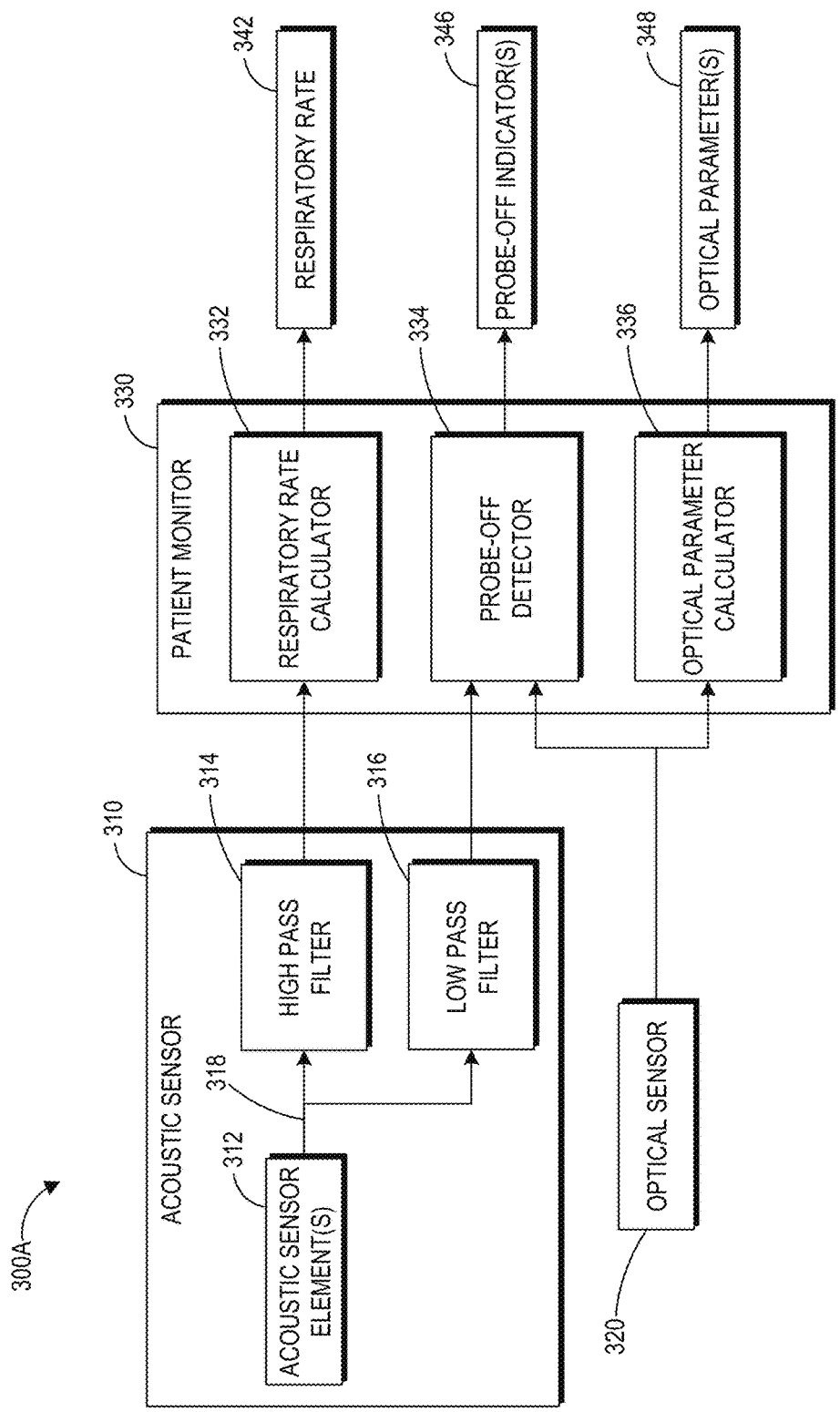
FIGS. 3A-C are block diagrams of example embodiments of patient monitoring systems with probe-off detection.
Figure 3B:
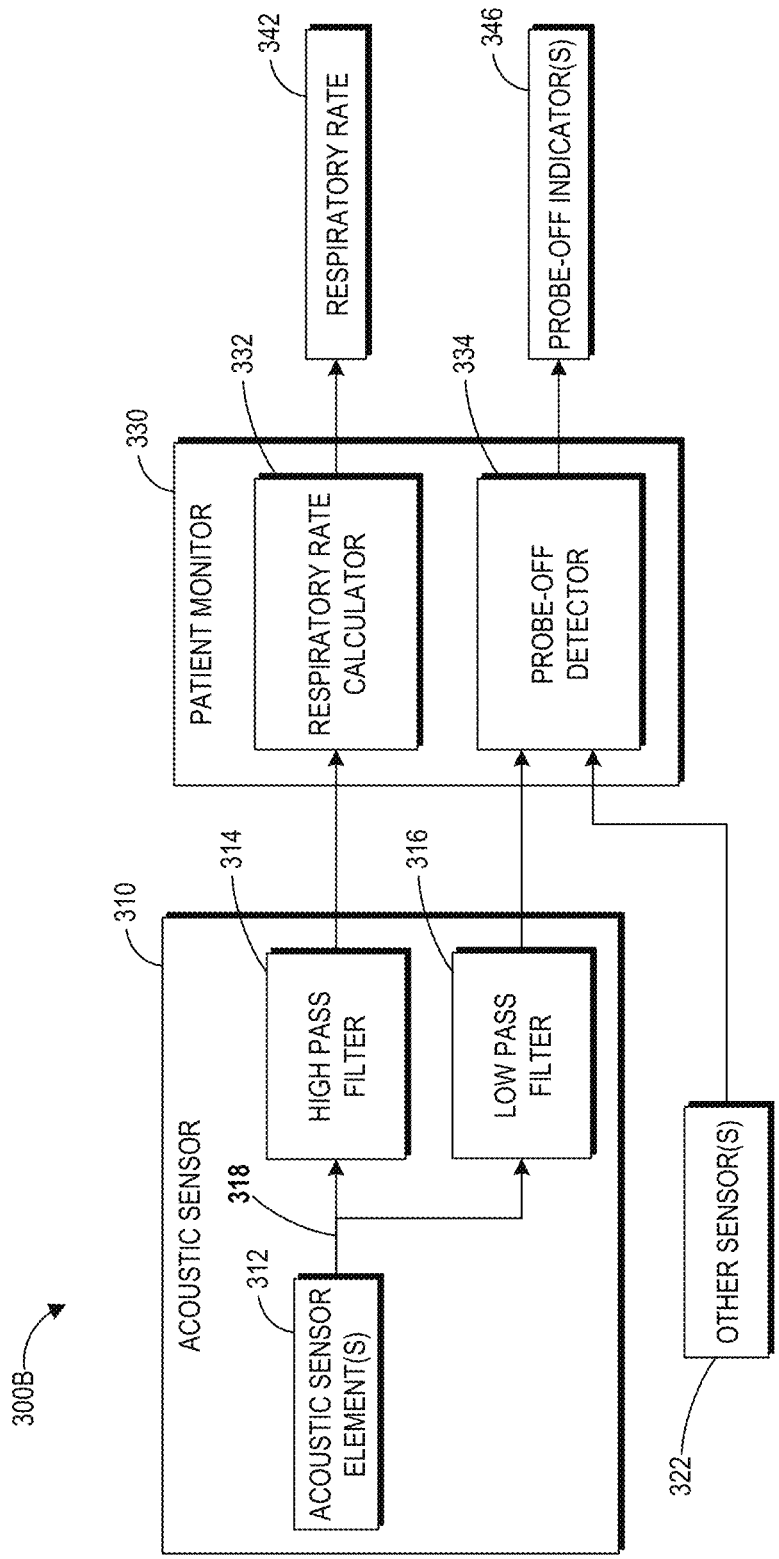
Figure 3C:
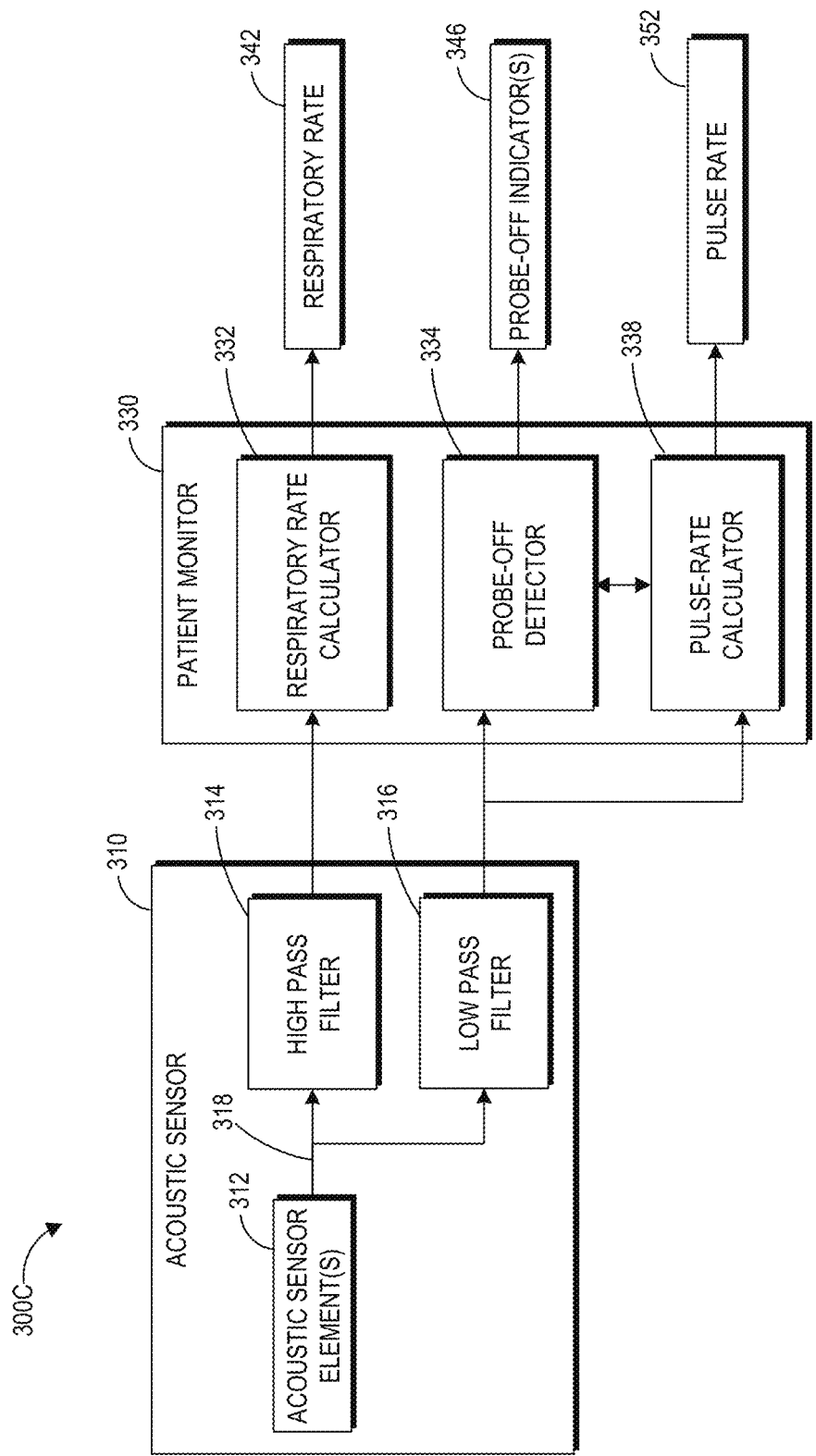

FIGS. 3A through 3C are block diagrams illustrating embodiments of patient monitoring systems 300 having probe-off detecting features. The probe-off detecting features can be useful for determining the connection state of the acoustic sensor on the patient.

FIG. 3A illustrates an embodiment of a patient monitoring system 300A. The patient monitoring system 300A includes an acoustic sensor 310, an optical sensor 320, and a patient monitor 330. The acoustic sensor 310 can include one or more acoustic sensor elements 312, such as any of the piezoelectric elements described above. In some embodiments, the acoustic sensor 310 can also include a high pass filter 314 and a low pass filter 316. In alternative embodiments, one or both of the filters 314 and 316 may be implemented in the patient monitor 330 instead or in addition to in the acoustic sensor 310.

In some embodiments, the acoustic sensor element(s) 312 produce one or more physiological signals indicative of one or more physiological sounds emanating from a patient's body. For example, the acoustic sensor elements 312 may produce a physiological signal that is indicative of a particular type of physiological sound, which is sometimes referred to herein as the target physiological sound. A variety of target physiological sounds are possible, for example, breathing or respiratory sounds, heart sounds, digestive sounds, vocalization and other speech sounds, and the like. For example, when an acoustic sensor is placed on the neck at or near the carotid artery, the target sounds can include both heart and respiratory sounds. The acoustic sensor 310 can also capture such sounds by being placed near an artery on the wrist, arm, or leg or may be placed on the chest directly over or near the heart.

The target sounds may occur in different frequency ranges. For example, respiratory sounds are typically found in a higher frequency range than heart sounds. Accordingly, it may be possible to select one or more target sounds by filtering frequency bands from the physiological signal 318. As such, the high pass filter 314 and low pass filter 316 can filter these frequency bands to separate heart sounds and respiratory sounds. The filters 314, 316 may be implemented in hardware (such as electronic circuitry) and/or software or firmware (such as in a processor).

In an embodiment, the high pass filter 314 selects a portion of the incoming signal corresponding to frequencies higher than a selected cut-off frequency. In one embodiment, the cut-off frequency of the high pass filter 314 can be selected so as to include respiratory sounds in a passband of the filter 314. These respiratory sounds may be in the range of about 100 Hz to about 1 kHz. Accordingly, the cutoff frequency can be at or below 100 Hz in one embodiment. However, higher or lower cutoff frequencies may be chosen for the high pass filter 314. The signal selected by the high pass filter 314 may be output to a respiratory rate calculator 332 of the patient monitor 330, which calculate and output the respiratory rate 342 of the patient.

The low pass filter 316 can select a portion of the incoming signal corresponding to frequencies lower than a cut-off frequency of the low pass filter 316. In one embodiment, the cut-off frequency of the low pass filter 316 is chosen so as to enable the filter 316 to select frequencies associated with heart rate or pulse rate sounds. Heart sounds typically have a frequency range lower than 3 Hz. A normal heart at rest beats at about 60 times a minute, or about once per second. Thus, in one embodiment, the cutoff frequency of the low pass filter 316 is about 3 Hz. Other values for the cut-off frequency are possible, such as, for example, about 5 Hz, 10 Hz, 20 Hz, or lower than 3 Hz. The signal output by the low pass filter 316 can be provided to a probe-off detector 334 of the patient monitor 330, which can provide an indication of any probe-off condition between the sensor and the patient, such as whether or not the sensor 310 is properly attached to the patient. Whether the sensor is properly attached to the patient may depend on the integrity of a connection between the acoustic sensor 310 and the patient. For example, the sensor 310 may be in some physical contact with the patient, but may not be fully attached to the patient or completely detached, resulting in false or weak signal measurements.

The patient monitor 330 can include hardware (such as one or more processors and/or electronic circuitry), software, and/or firmware for measuring a physiological parameter such as respiratory rate. Inputs to the parameter calculator 110 can include, among others, optical sensor data provided by the optical sensor 320 and the outputs of the filters 314, 316 described above.

The optical sensor 102 can be a pulse oximetry sensor, a co-oximetry sensor, or the like. The optical sensor 320 can use spectrophotometry techniques to measure a variety of blood constituents, including for example, oxygen saturation, hemoglobin, methemoglobin, carboxyhemoglobin, other hemoglobin species, concentrations of the same, and the like. In addition, the optical sensor 320 can also be used to measure a variety of other physiological parameters, including pulse rate, perfusion, and the like. The optical sensor 320 can include one or more emitters that shine one or more wavelengths of light through tissue of a living person, such as through a finger, toe, or foot. One or more detectors can receive the transmitted light after attenuation by the tissue and can generate one or more signals responsive to the attenuated light.

The optical sensor 102 may operate at one or more wavelengths. In one embodiment, the optical sensor 102 operates at a single wavelength, e.g., using a single emitter (or multiple emitters of the same wavelength) to produce a photoplethysmograph output. However, the optical sensor 102 may also operate at multiple wavelengths to generate a photoplethysmograph. The photoplethysmograph (sometimes referred to herein as a "plethysmograph," "photopleth," "pleth" or "PPG") can be a waveform that represents changes in blood volume as measured by one or more wavelengths of light irradiated at a tissue site of a patient. These changes in blood volume can be caused by arterial pulsation, and as such, can be related to pulse rate. Thus, the photoplethysmograph can include pulse rate information, which the parameter calculator 336 can analyze to derive an indication of pulse rate for a patient.

Advantageously, in certain embodiments, the probe-off detector 334 of the patient monitor 330 can use the optical sensor data (including photpleth data) together with the acoustic sensor output of the low pass filter 316 to detect a probe-off condition of either sensor 310, 320. In one embodiment, the probe-off detector 334 can use the optical sensor data and the selected portion of the physiological signal from the low pass filter 316 to provide an indication 346 as to the quality of the connection between the acoustic sensor 310 and the patient, such as whether or not the sensor 310 is properly attached to the patient. For example, if the output of the low pass filter 316 includes sounds corresponding to pulse rate and the photoplethysmograph includes pulse rate information, the probe-off detector 334 can consider the acoustic sensor 310 and optical sensor 320 to be properly attached. If the output of the low pass filter 316 does not include a detectable pulse rate and the photopleth does (as detected by the probe-off detector 334), the probe-off detector 334 may conclude that the acoustic sensor is not properly attached and output a probe off indication 346 accordingly. Similarly, if the probe-off detector 334 detects pulse rate in the output of the low pass filter 316 but not in that of the photopleth, the probe-off detector 334 can output a probe-off indicator 346 that indicates the optical sensor 320 may not be properly attached. In some embodiments, instead of outputting a probe-off indicator 346, the probe-off detector can output a check sensor placement indicator.

The probe-off detector 334 can compare the output of the two sensors 310, 320 in a variety of ways to determine whether either sensor 310, 320 is in a probe-off state. For instance, the probe-off detector 334 can correlate the signals from the optical sensor 320 and acoustic sensor 310 to determine connection quality or probe on/off condition of the acoustic sensor 310. In one embodiment, this correlation involves comparing the pulse rate obtained from both sensors. If the pulse rate is obtained from both sensors and it is similar or within a threshold, then there is a high likelihood that one or both of the sensors are properly attached to the patient, and the probe-off detector 334 does not output a probe-off condition. In another embodiment, the probe-off detector 334 can calculate a cross-correlation (or convolution or other similar calculation, in either the time or frequency domain) between the signals obtained from the optical sensor 320 and the acoustic sensor 310. The probe-off detector 334 can indicate that a probe-off condition exists if the area under the cross-correlated signal is above a certain threshold or if there are peaks in the cross-correlated spectrum above a certain threshold. In some embodiments, the probe-off detector 334 outputs an indication for the connection state of the sensor for displayed on a display connected to the patient monitor 330. The output can also include an audible and/or visual alarm. An example of indicator is described below with respect to FIG. 13.

In other embodiments (not shown), the high pass filter 314 and low pass filter 316 may be omitted from the acoustic sensor 310. Instead, the output of the acoustic sensor elements 312 can be provided directly to the probe-off detector 334, which can attempt to detect pulse rate in this output. Similarly, the output of the acoustic sensor elements 312 can be provided to the respiratory rate calculator 332, which can calculate respiratory rate from this output.

FIG. 3B illustrates another embodiment of a probe-off monitoring system 300B. In the depicted embodiment, the patient monitoring system 300B includes the acoustic sensor 310 of FIG. 3A and one or more other sensors 322. The one or more other sensors 322 can include, for example, one or more additional acoustic sensors, ECG sensors, electroencephalography (EEG) sensors, optical sensors, and/or bioimpedance sensors. The one or more other sensors 322 may be positioned at various locations on the patient's body (see, e.g., FIG. 4).

In some embodiments, the other sensor 322 is a second acoustic sensor. The second acoustic sensor can be placed in a second location on the patient's body apart from the location of the acoustic sensor 310. For example, if the acoustic sensor 310 is placed on the patient's neck, the second acoustic sensor can be placed over the heart, wrist (e.g., over the ulnar or radial artery), leg, chest, back, etc. of the patient. Alternatively, two acoustic sensors (310, 322) can be placed together in one location. The one or more sensors 322 may also include a third (or more) acoustic sensor(s). The third acoustic sensor can be placed at or near an artery at a different location.

The acoustic sensor 310 and one or more other sensors 322, for example, can be coupled to the probe-off detector 334. The low pass filter 316 can select the portion of the physiological signal 318 corresponding to a patient's heart sound or pulse rate. The one or more other sensors 322 can output a second physiological signal that is provided to the probe-off detector 334. If the other sensor 322 includes an acoustic sensor, the acoustic sensor may also include a loss pass filter that outputs a filtered signal including heart rate information. The probe-off detector 334 can correlate the physiological signal 318 from the acoustic sensor 310 with a second physiological signal to determine probe off/on of the acoustic sensor 310.

In some embodiments, the probe-off detector can also use physiological signals from other sensors, for example, an ECG sensor, or an EEG sensor. In one embodiment, the signal from the ECG sensor can be used to calculate pulse rate of the patient by the probe-off detector 334. The pulse rate can be then compared with that obtained from the acoustic sensor 310. If the measured pulse rate from the acoustic sensor is substantially similar to the measured pulse rate from the ECG sensor, as determined by the probe-off detector 334, then an indication of probe-on condition may be optionally displayed on the monitor. If the two rates are, however, not within a threshold value, an indication of probe-off condition may be displayed on the monitor. Other algorithms can be used to correlate the output of the two (or more) sensors 310, 322, as will be described in greater detail below. Likewise, the other sensor(s) 322 can include an EEG sensor that includes pulse oximetry functionality for detecting pulse rate, which the probe-off detector 334 can correlate to determine probe-off or on conditions.

FIG. 3C illustrates another embodiment of a patient monitoring system 300C. In the depicted embodiment, the patient monitoring system 300C can determine probe-off or probe-on condition of the acoustic sensor 310 without using one or more other sensors 320, 322 of FIGS. 3A and 3B. As in FIGS. 3A and 3B, the low-pass filter 316 can output a filtered signal that may include heart rate information. The patient monitor 330 includes, in addition to the respiratory rate calculator 332 and probe-off detector 334, a pulse rate calculator 338 that can attempt to calculate a pulse rate from the output of the low pass filter 316. The pulse rate calculator 338 can provide an indication of whether a pulse rate was detected to the probe-off detector 334, which can determine from this information whether the acoustic sensor 310 is properly connected. If a pulse rate is not detected, the probe-off detector 334 can output a probe-off indicator. In addition, the pulse rate calculator 338 may also output the calculated pulse rate 352 on a display of the patient monitor 330. In some embodiments, instead of outputting a probe-off indicator, the probe-off detector can output a check sensor placement indicator (see, e.g., FIG. 14B).

Figure 4:
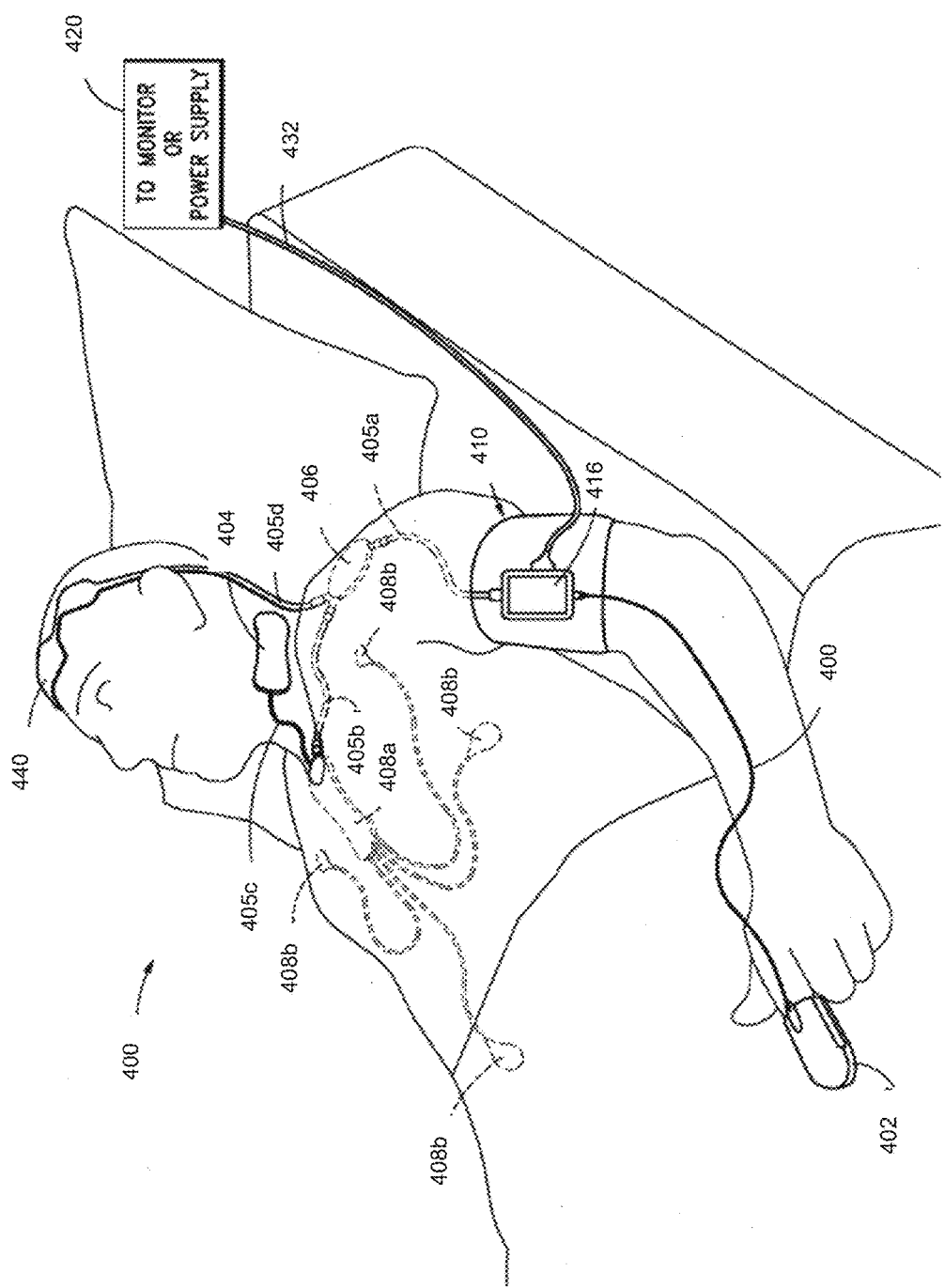
FIG. 4 illustrates a further embodiment of a patient monitoring system.

FIG. 4 illustrates another embodiment of a patient monitoring system 400. The features of the patient monitoring system 400 can be combined with any of the features of the systems described elsewhere herein. Likewise, any of the features described elsewhere herein can be incorporated into the patient monitoring system 400. In the depicted embodiment, the patient monitoring system 400 includes a cable hub 406 that enables one or many sensors to be selectively connected and disconnected to the cable hub 406.

The monitoring system 400 includes a cuff 410 with a patient device 416 for providing physiological information to a patient monitor 420 or which can receive power from a power supply (420). The patient monitor 420 can implement any of the functionality of the patient monitors 330 described above. The cuff 410 can be a blood pressure cuff or merely a holder for the patient device 416. The patient device 416 can instead be a wireless transceiver. The patient device 416 is also coupled with an optical finger sensor 402 via cable 407. Further, the patient device 416 is coupled with the cable hub 406 via a cable 405a. The cable hub 406 can be selectively connected to one or more sensors. In the depicted embodiment, example sensors shown coupled to the cable hub 406 include an ECG sensor 408a and a brain sensor 440. The ECG sensor 408a can be single-lead or multi-lead sensor. The brain sensor 440 can be an electroencephalography (EEG) sensor and/or an optical sensor. An example of EEG sensor that can be used as the brain sensor 440 is the SEDLine™ sensor available from Masimo® Corporation of Irvine, Calif., which can be used for depth-of-anesthesia monitoring among other uses. Optical brain sensors can perform spectrophotometric measurements using, for example, reflectance pulse oximetry. The brain sensor 440 can incorporate both an EEG/depth-of-anesthesia sensor and an optical sensor for cerebral oximetry.

The ECG sensor 408a is coupled to an acoustic sensor 404 and one or more additional ECG leads 408b. For illustrative purposes, four additional leads 408b are shown, for a 5-lead ECG configuration. In other embodiments, one or two additional leads 408b are used instead of four additional leads. In still other embodiments, up to at least 12 leads 408b can be included. Acoustic sensors can also be disposed in the ECG sensor 408a and/or lead(s) 408b or on other locations of the body, such as over a patient's stomach (e.g., to detect bowel sounds, thereby verifying patient's digestive health, for example, in preparation for discharge from a hospital). Further, in other embodiments, the acoustic sensor 404 can connect directly to the cable hub 406 instead of to the ECG sensor 408a.

The cable hub 406 can enable one or many sensors to be selectively connected and disconnected to the cable hub 406. It can be advantageous to obtain physiological signals from multiple sensors to determine probe-off conditions, e.g., by correlation as described above. For example, a signal from the acoustic sensor 404 can be correlated with a signal from the ECG sensor 408. The cable hub can enable capturing signals from multiple sensors for correlation. Advantageously, in certain embodiments, the correlation from multiple sensors can enable indication of a probe-off condition.

IV. Example Waveforms

Figure 5:
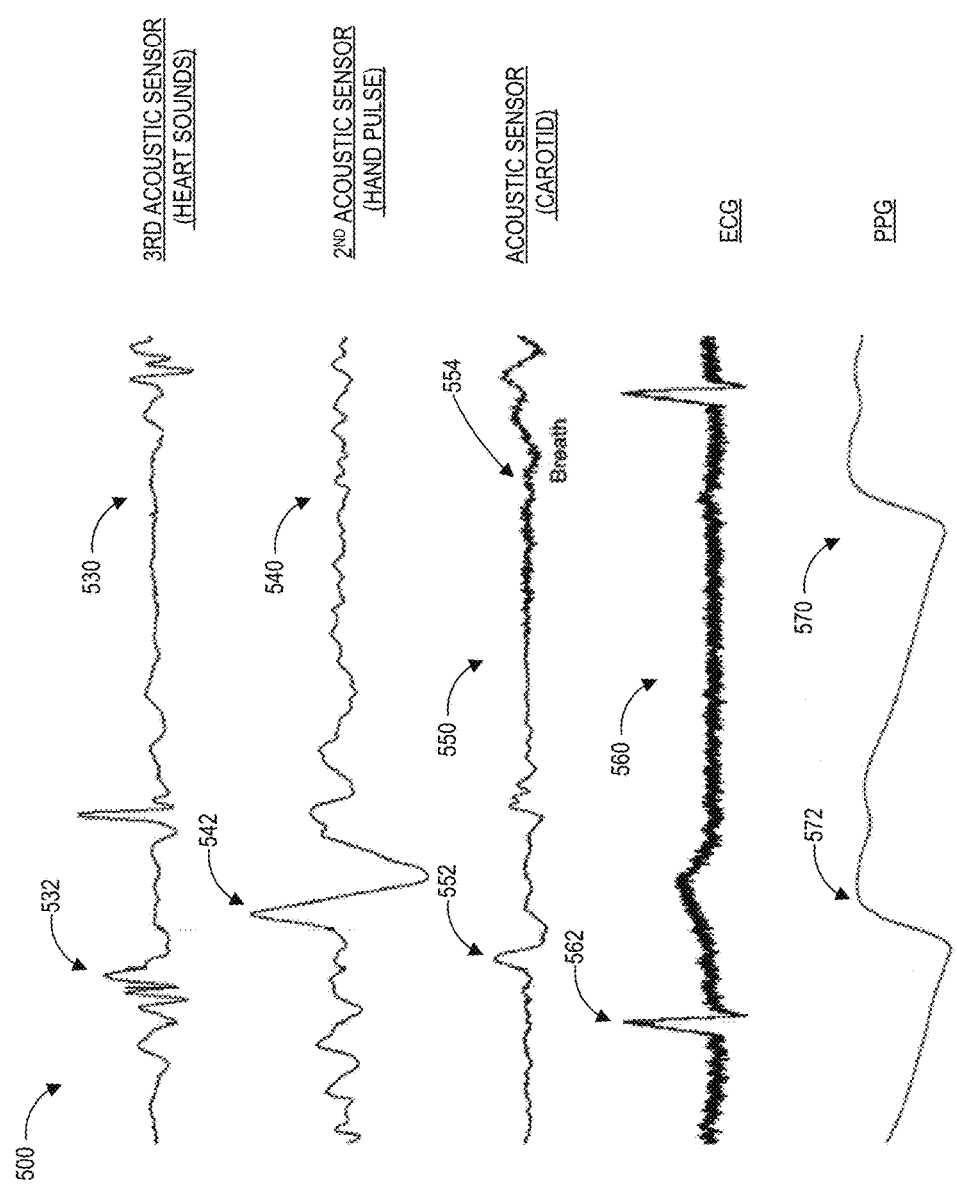
FIG. 5 illustrates plots of example acoustic waveforms that can be used to identify probe-off condition.

Turning to FIG. 5, a plot 500 is shown that includes a set of five example waveforms. An acoustic heart sounds waveform 530 and the acoustic wrist pulse waveform 540 are illustrated, along with a third acoustic waveform (an acoustic carotid pulse waveform) 550 and an ECG waveform 560. The plot 500D helps to illustrate the correlation performed by the probe-off detector in certain embodiments. The use of two sensors results in two physiological signals, which can be correlated to identify the connection state of one of the sensors.

In one embodiment, the physiological signal 250 from the acoustic sensor 310 of FIGS. 3A-B can be correlated with the plethysmograph waveform 570. For example, the peak 572 of the plethysmograph waveform 570 can be correlated with the peak 552 of the physiological signal 550 from the acoustic sensor in accordance with the system of FIG. 3A. Depending on the success of correlation, the probe-off detector 334 of FIGS. 3A-B can determine the connection quality of the acoustic sensor 310. Correlating peaks can be done by cross-correlation algorithms and signal processing.

In another embodiment, the physiological signal 250 from the acoustic sensor 310 of FIGS. 3A-B can be correlated with one or more of the physiological signals 530, 540, or 560. For example, the peak 532 of the third physiological signal 530 from the third acoustic sensor 530 can be correlated with the peak 552 of the physiological signal 550 from the acoustic sensor in accordance with the system of FIG. 3B. Similarly, the peak 542 of the second physiological signal 540 can be correlated with the peak 552 of the physiological signal 550 from the acoustic sensor. These peaks represent or are related to heart rate of the patient. In some implementations, the physiological signal 550 from the acoustic sensor can be correlated with more than one of the signals 530, 540, 560, or 570.

V. Probe-Off Detection Process

Figure 6:
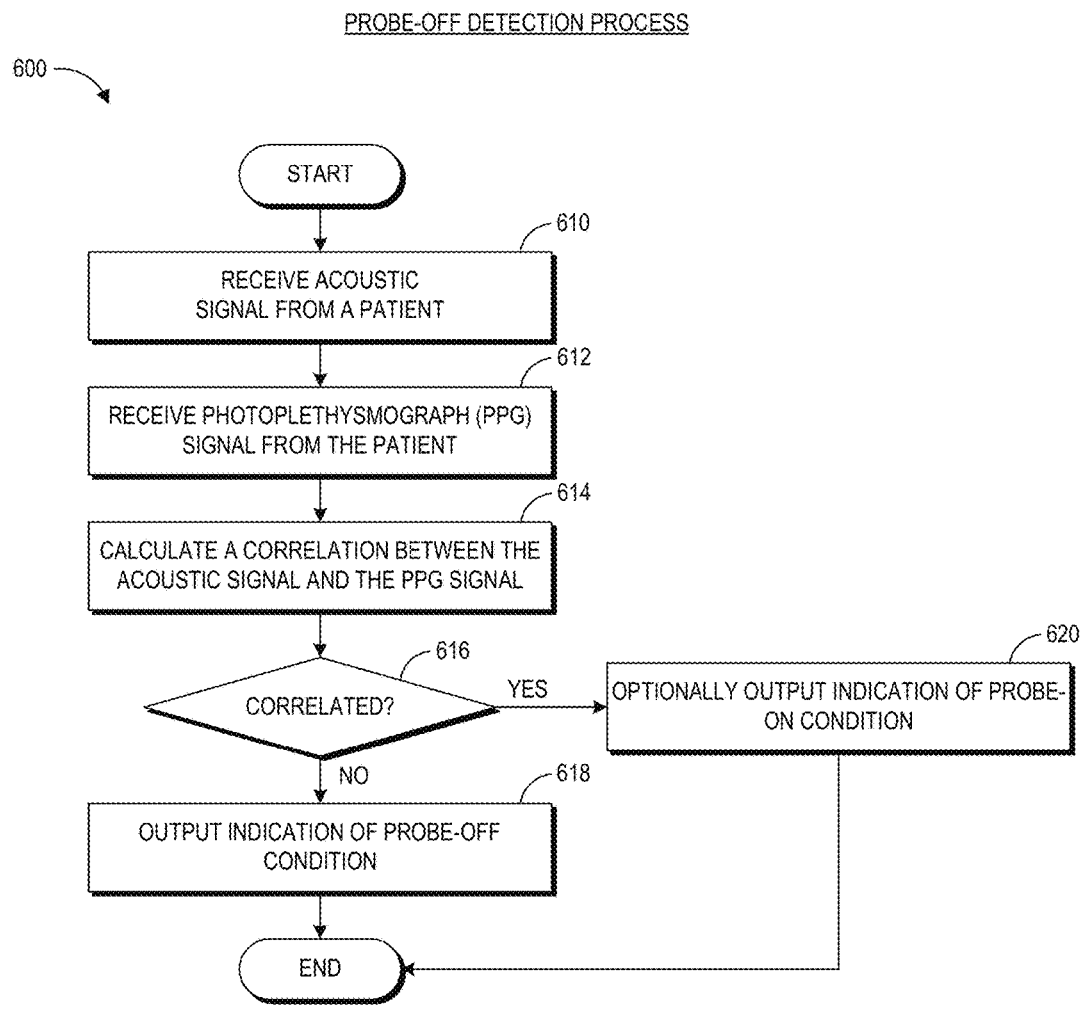
FIGS. 6, 7A-B, 8 illustrate embodiments of processes for identifying the probe-off condition.
Figure 7A:
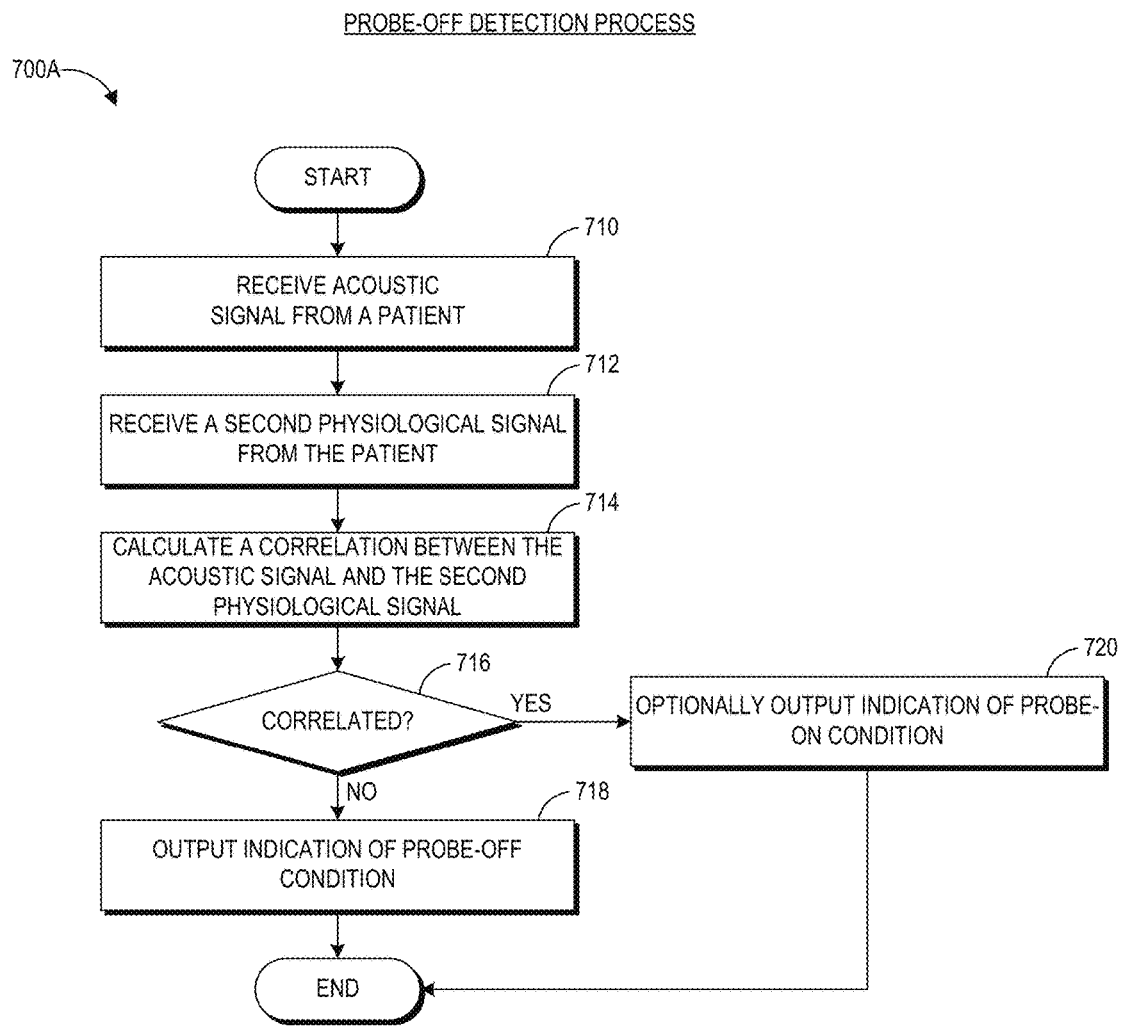
Figure 7B:
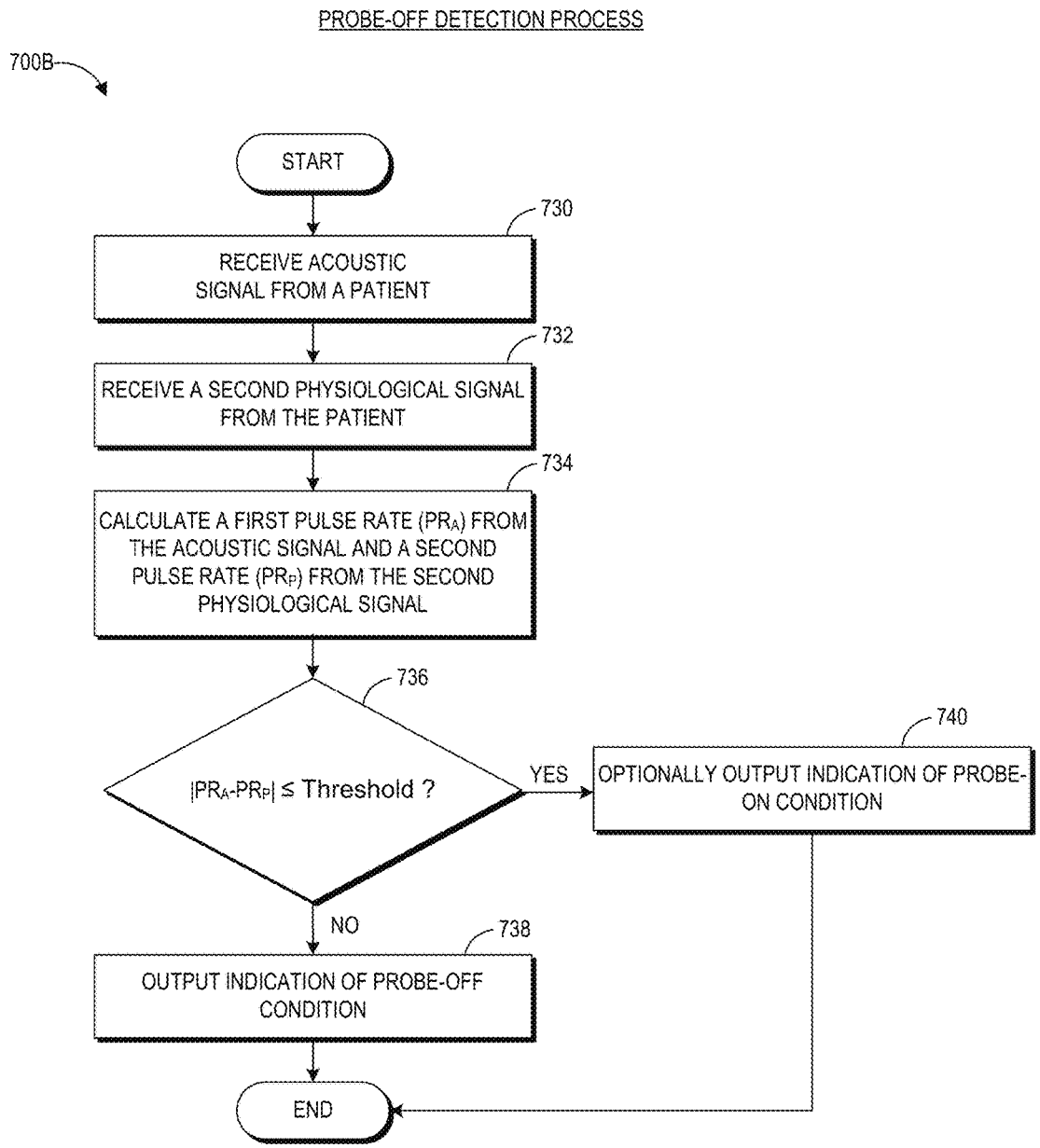
Figure 8:
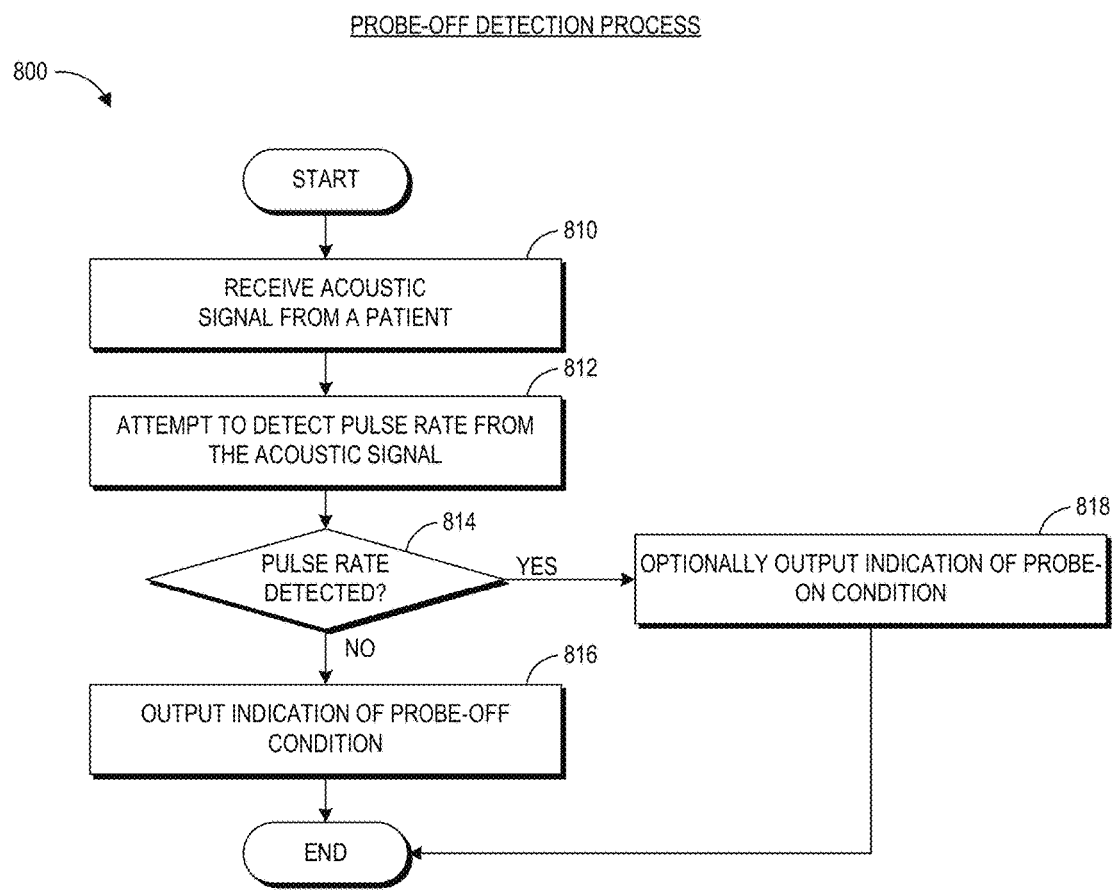

FIGS. 6, 7, and 8 illustrate embodiments of processes 600, 700, and 800 respectively for determining whether the sensor is properly attached to the patient. These processes can be implemented by any of the systems 100, 300, 400 described above. In particular, each of these processes can be implemented by any of the probe-off detectors 334 described above. Advantageously, in certain embodiments, these processes can determine, based at least partly on non-invasive physiological measurements, whether to trigger an indication of a probe-off condition.

Referring specifically to FIG. 6, at block 610, a first physiological acoustic signal is received from an acoustic sensor coupled to the patient. Similarly, a photoplethysmograph signal is received from the patient through an optical sensor at block 612. The probe-off detector 334 calculates a correlation at block 614 between the acoustic signal and the photoplethysmograph signal as described above. At block 616, the probe-off detector 334 determines based on the calculation whether the two signals are correlated. If the two signals are correlated, then in an optional step at block 620, an output indication of successful connection condition is sent. This correlation can include computing a cross-correlation, convolution, or the like as described above. The correlation can be done in the time domain or the frequency domain. Correlation can also include calculating a Pearson correlation coefficient based on both signals. In the alternative, if the two signals are not correlated, then an output indication of probe-off condition is sent at block 618.

FIG. 7A illustrates another embodiment of a process 700A for determining whether a sensor is properly attached to a patient. At block 710, a first physiological acoustic signal is received from an acoustic sensor coupled to the patient. Similarly, a second physiological signal is received from the patient through an optical sensor at block 712. The probe-off detector calculates a correlation at block 714 between the acoustic signal and the second physiological signal as described above. At block 716, the probe-off detector determines based on the calculation whether the two signals are correlated, e.g., as described above. If the two signals are correlated, then in an optional step at block 720, an output indication of successful connection condition is sent. In the alternative, if the two signals are not correlated, then an output indication of a probe-off condition is sent at block 718.

FIG. 7B illustrates yet another embodiment of a process 700B for determining whether a sensor is properly attached to a patient. At block 730, an acoustic signal is received from a patient, and at block 732, a second physiological signal is received from the patient (using any other sensor). At block 734, the probe-off detector 334 calculates a first pulse rate ($PR_A$) from the acoustic signal and a second pulse rate ($PR_P$) from the second physiological signal. The probe-off detector 334 then determines, at block 736, whether an absolute value of the difference between the two pulse rates is within a threshold value. If so, the probe-off detector 334 can optionally output an indication of a probe-on condition at block 740. If not, the probe-off detector 334 can output an indication of a probe-off condition at block 738.

The process 700B can therefore facilitate rapid and processing resource efficient calculation of a probe-off (or on) condition because, instead of performing a cross-correlation or the like, the process 700B obtains the difference between the two pulse rate calculations. However, in certain embodiments, the features of the process 700B can be combined with any of the other processes described herein. For instance, the probe-off detector 334 can implement the features of the process 700B as well as calculate the cross-correlation between the two signals as described above. The probe-off detector 334 can use both the cross-correlation and the difference between the two calculated pulse rates to determine whether a probe-off condition is present. Additional embodiments for combining the output of different algorithms are described in greater detail below.

FIG. 8 illustrates an embodiment of a process 800 for determining whether the sensor is properly attached to the patient. At block 810, a physiological acoustic signal is received from an acoustic sensor coupled to the patient. The pulse rate calculator and the probe-off detector independently or in combination, attempt to detect a pulse rate from the received signal at block 812. At block 814, the probe-off detector determines whether a pulse is detected. If the pulse is detected, then in an optional step at block 818, an output indication of successful connection condition is sent. In the alternative, if the pulse is not detected, then an output indication of a probe-off condition is sent at block 816. Effectively, the process 800 determines whether the sensor is properly attached to the patient with respect to the embodiments described in FIG. 3C.

Figure 9:
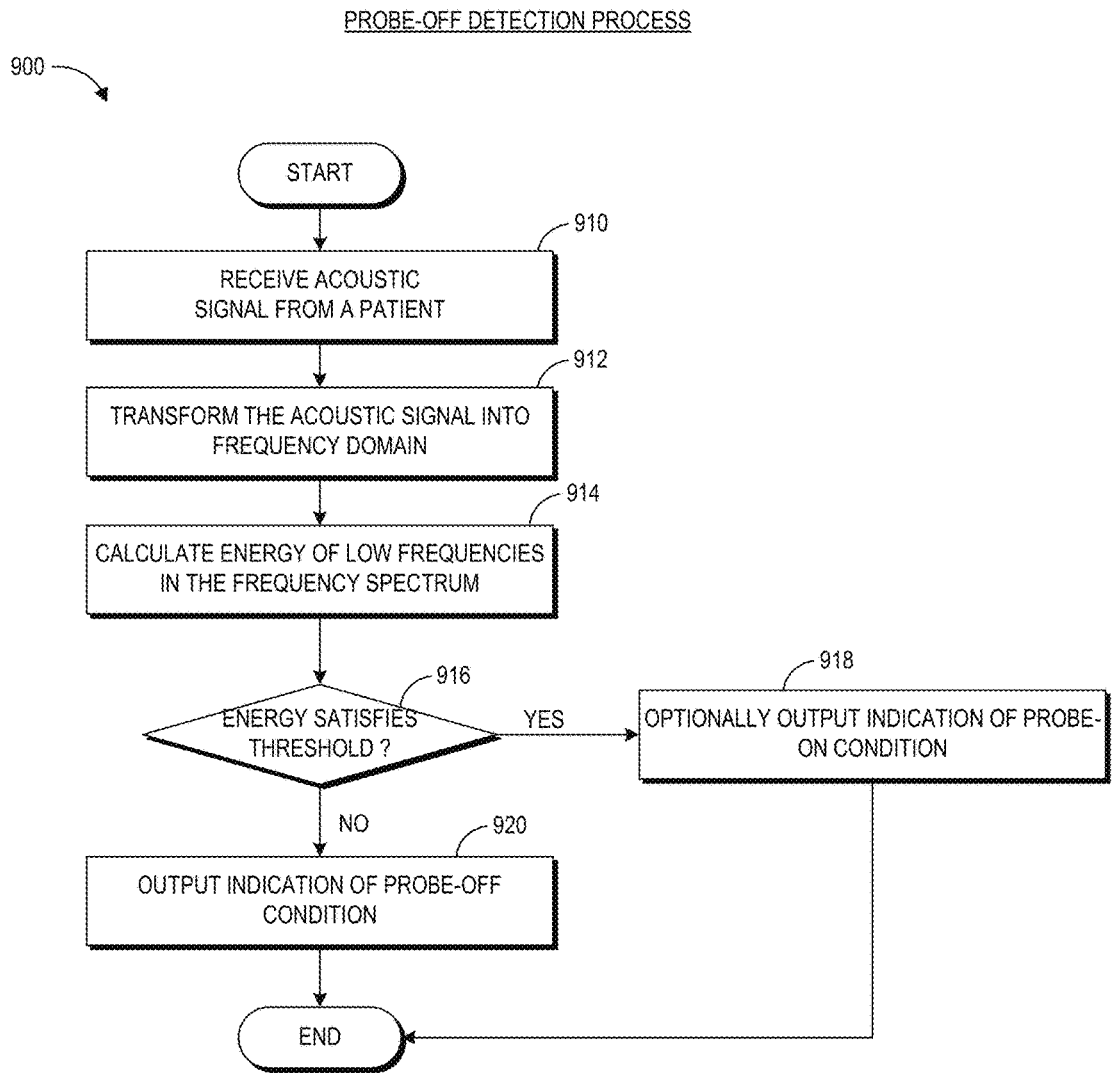
FIG. 9 illustrates an embodiment of processes for identifying the probe-off condition.

FIG. 9 illustrates an embodiment of a process 900 for determining whether the sensor is properly attached to the patient. At block 910, a physiological acoustic signal is received from an acoustic sensor coupled to the patient. The acoustic signal is transformed into a frequency domain equivalent transformed signal at block 912. In one embodiment, a fast Fourier transform ("FFT") of the acoustic signal generates the transformed frequency domain signal, producing a signal having a plurality of frequency bins. At block 914, the energy in the low frequency bins is calculated. Energy in the low frequency bins can reflect the presence of heart rate. In one embodiment, the energy in the lowest frequency bin is calculated. In another embodiment, the energy in a plurality of the lowest frequency bins are calculated. The energy can be calculated by taking the magnitude of the FFT signal. Alternatively, the power in each bin can be calculated by computing the power spectral density of the acoustic signal.

If the energy is calculated from multiple bins, the sum of the energy may be computed to compute an overall energy for a plurality of bins. If the energy (or overall energy) in the low frequency bin or bins meets or exceeds a threshold value, then in an optional step at block 918, an output indication of successful connection condition is sent. In the alternative, if the pulse is not detected, then an output indication of a probe-off condition is sent at block 920.

VI. Using Pulse Shape Information to Detect Pulse Rate in an Acoustic Sensor

Figure 10:
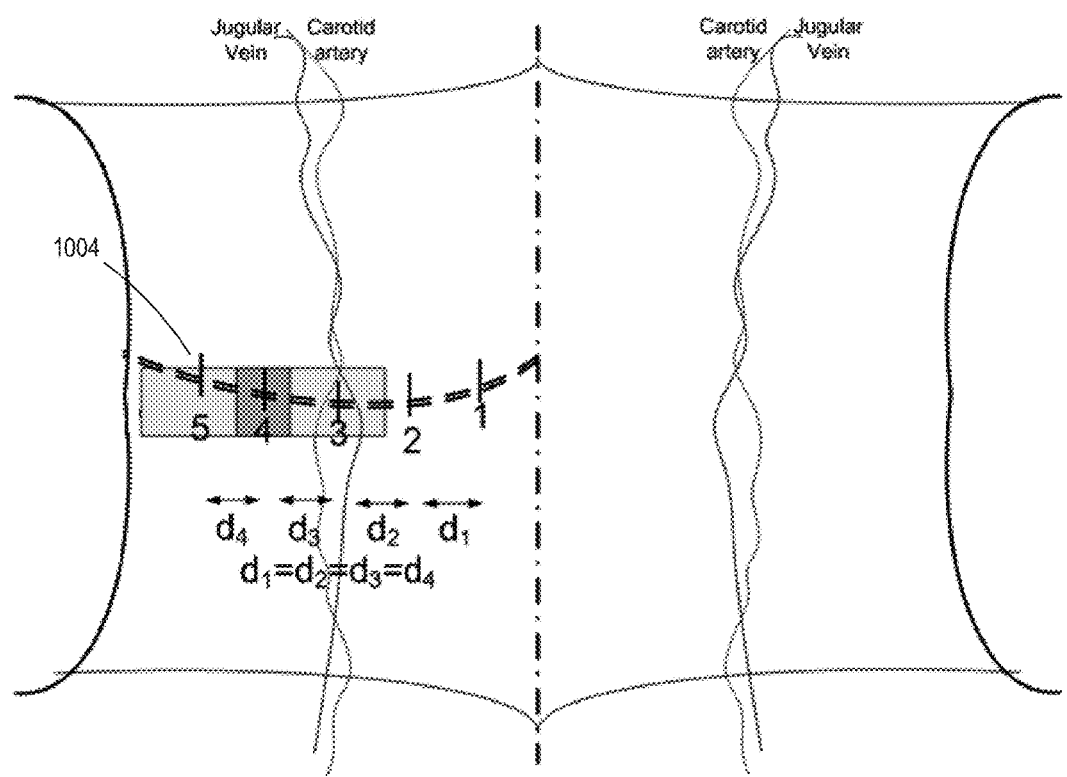
FIG. 10 illustrates example features for improving the location accuracy of an acoustic sensor.

Other algorithms than those described above can be used to detect pulse rate, and therefore a probe-on (or off) condition, in an acoustic sensor. Some additional examples of such algorithms are described below. Further, it can be useful to obtain a more accurate indication of where on the neck an acoustic sensor should be placed to more accurately detect the carotid pulse. Placing the acoustic sensor directly over the carotid artery, for instance, may result in a higher signal to noise ratio (SNR) for detecting pulse rate than if the acoustic sensor is placed elsewhere. Improving SNR for detecting pulse rate can improve the accuracy of probe-off detection algorithms implemented by the systems described herein. FIG. 10 illustrates example features for improving the location accuracy of an acoustic sensor. FIGS. 11A through E illustrate various patterns of detected pulse rates for different patients based on neck placement. Using these patterns, an algorithm can be constructed that attempts to match an individual patient's pulse rate patterns to one or more pulse rate patterns of many patients to further improve pulse rate detection and therefore probe-off detection accuracy. FIG. 12 depicts an example algorithm that the probe-off detector 334 described above can use pattern matching for probe-off detection.

Referring to FIG. 10, an acoustic sensor 1004 is shown placed over the neck of a patient in the proximity of the jugular vein or the carotid artery at a first position. The positions described here are with respect to the location of the artery or the vein. One or more acoustic signals may be obtained at this first position. The acoustic sensor 1004 is then moved to different positions with respect to the carotid artery or the jugular vein as shown in FIG. 10. One or more acoustic signals may be obtained at multiple positions over the neck of a patient in the proximity of the jugular vein or the carotid artery. These measurements may be repeated for a group of subjects. In one embodiment, the measurements are obtained for a group of five or more subjects. Although not shown, a laser interferometer may be used to detect where on the patient's skin the highest peak vibrations are corresponding to pulse rate, and this interferometer data can be compared and/or correlated with the acoustic sensor data to improve placement of the acoustic sensor on a patient.

Figure 11A:
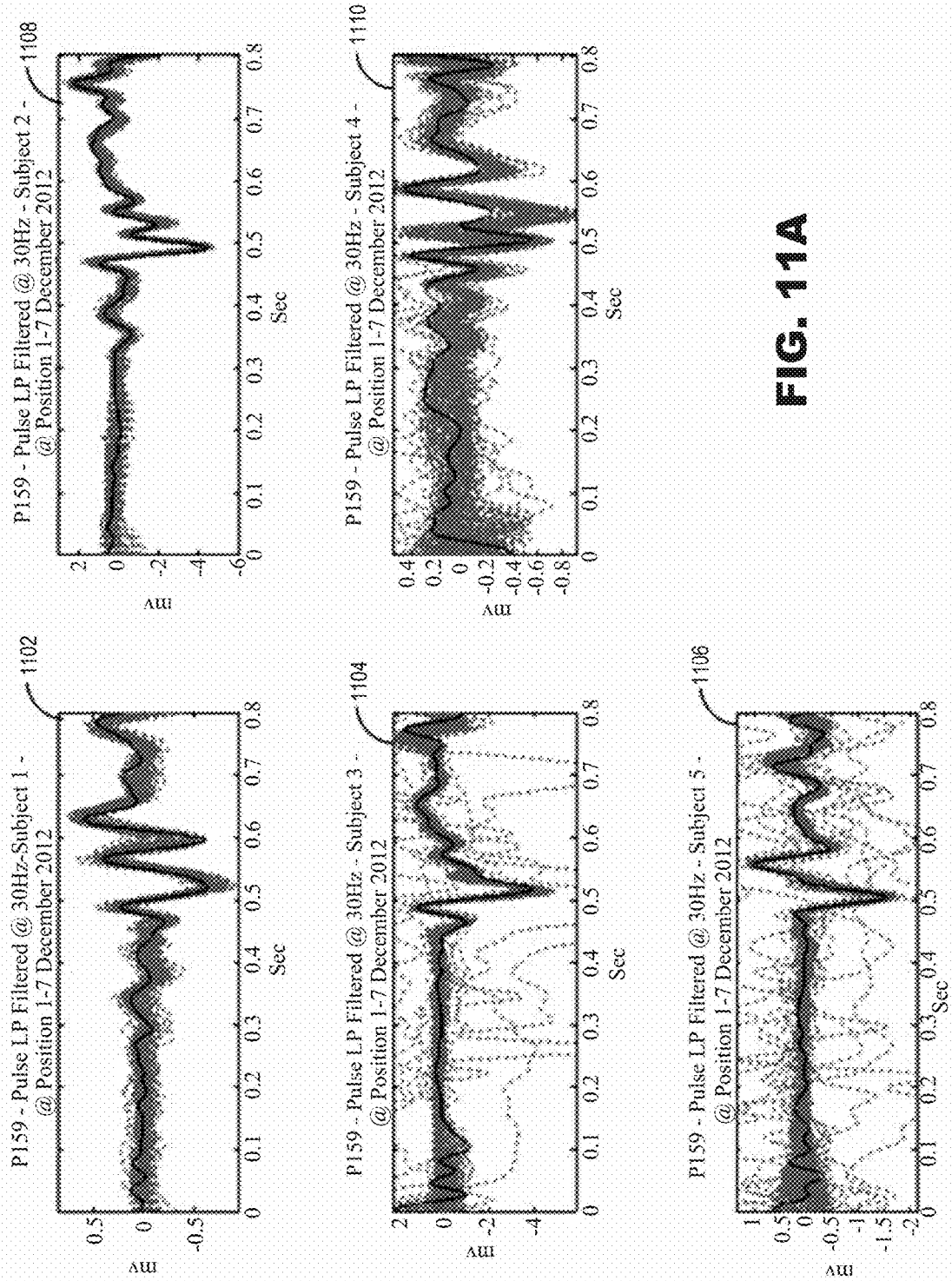
FIGS. 11A-E illustrate various patterns of detected pulse rates for different patients based on neck placement.

FIGS. 11A through E illustrate example acoustic waveforms obtained at different positions (e.g., as shown schematically in FIG. 10) as the sensor is placed over the neck of the five subjects. For example, FIG. 11A shows acoustic pulse waveforms 1102 at a first position for a first subject. Acoustic waveform 1104 corresponds to a second subject at the first position. Likewise, acoustic pulses 1106, 1108, and 1110 correspond to a third, fourth, and a fifth subject, respectively with all of the measurements taken at the first position.

Figure 11B:
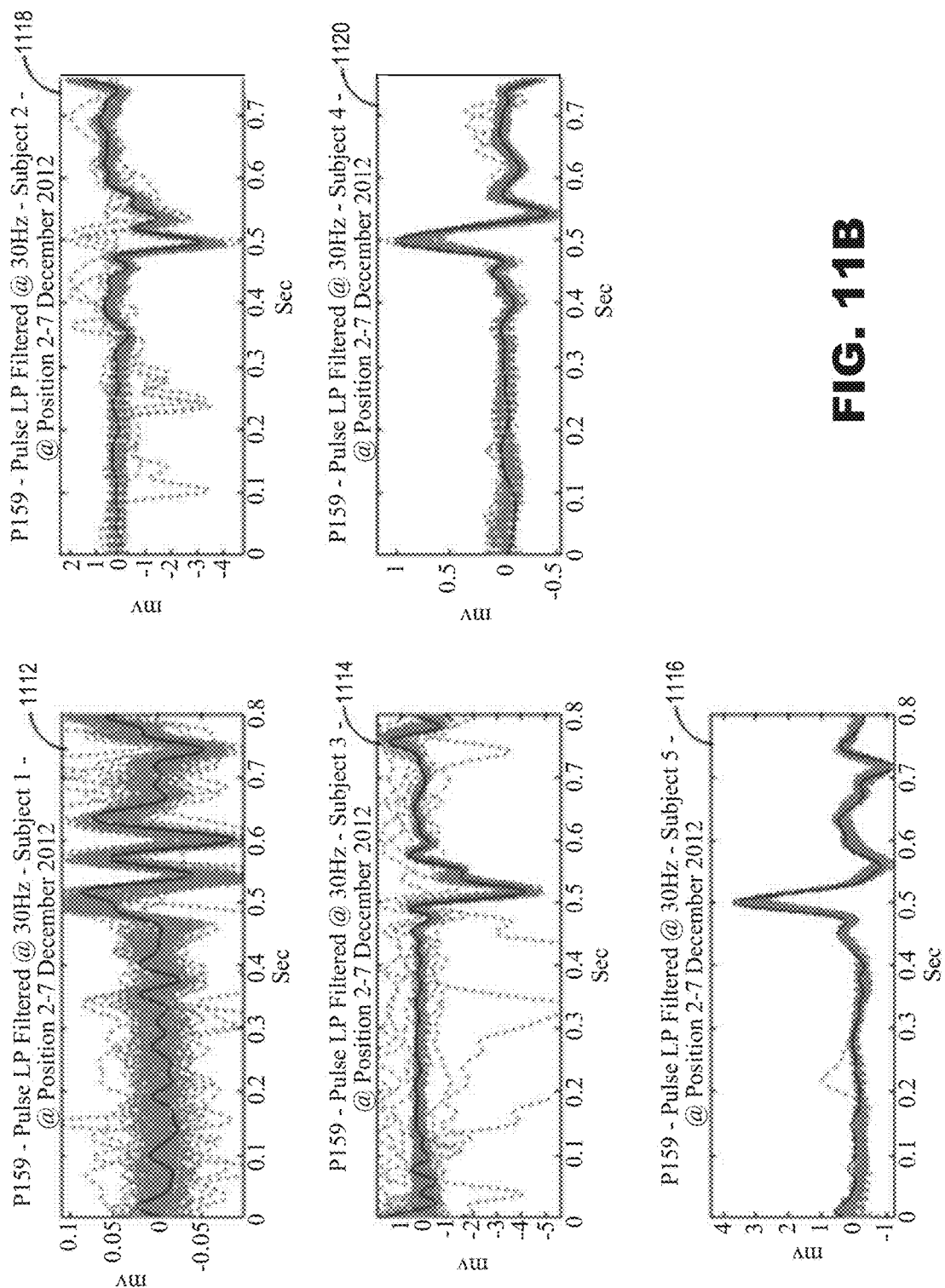

Waveforms 1112, 1114, 1116, 1118, and 1120 in FIG. 11B correspond to acoustic pulses for a first, second, third, fourth, and a fifth subject, respectively at a second position. Similarly, waveforms shown in FIGS. 11C-E correspond to the group of five subjects at different positions. In one embodiment, the group of five subjects remains the same between positions. In another embodiment, the group of five subjects may be different.

At some of these positions, the variation between the acoustic waveforms between the subjects may vary significantly. The signal may also be noisy and may not contain distinctive features. For example, in FIG. 11A and FIG. 11E, the variation between waveforms 1102, 1104, 1106, 1108, and 1110 may be significant.

Figure 11C:
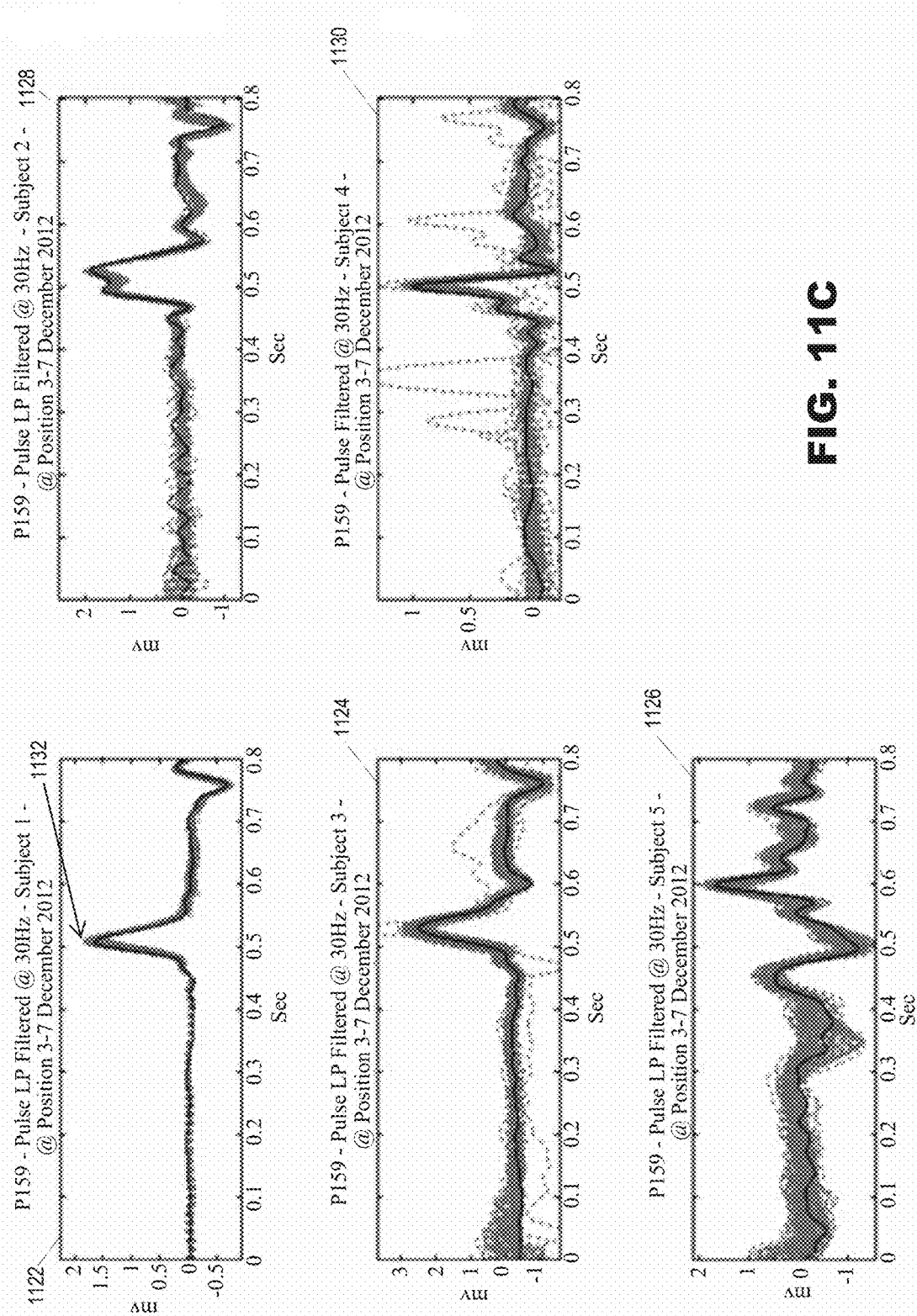
Figure 11D:
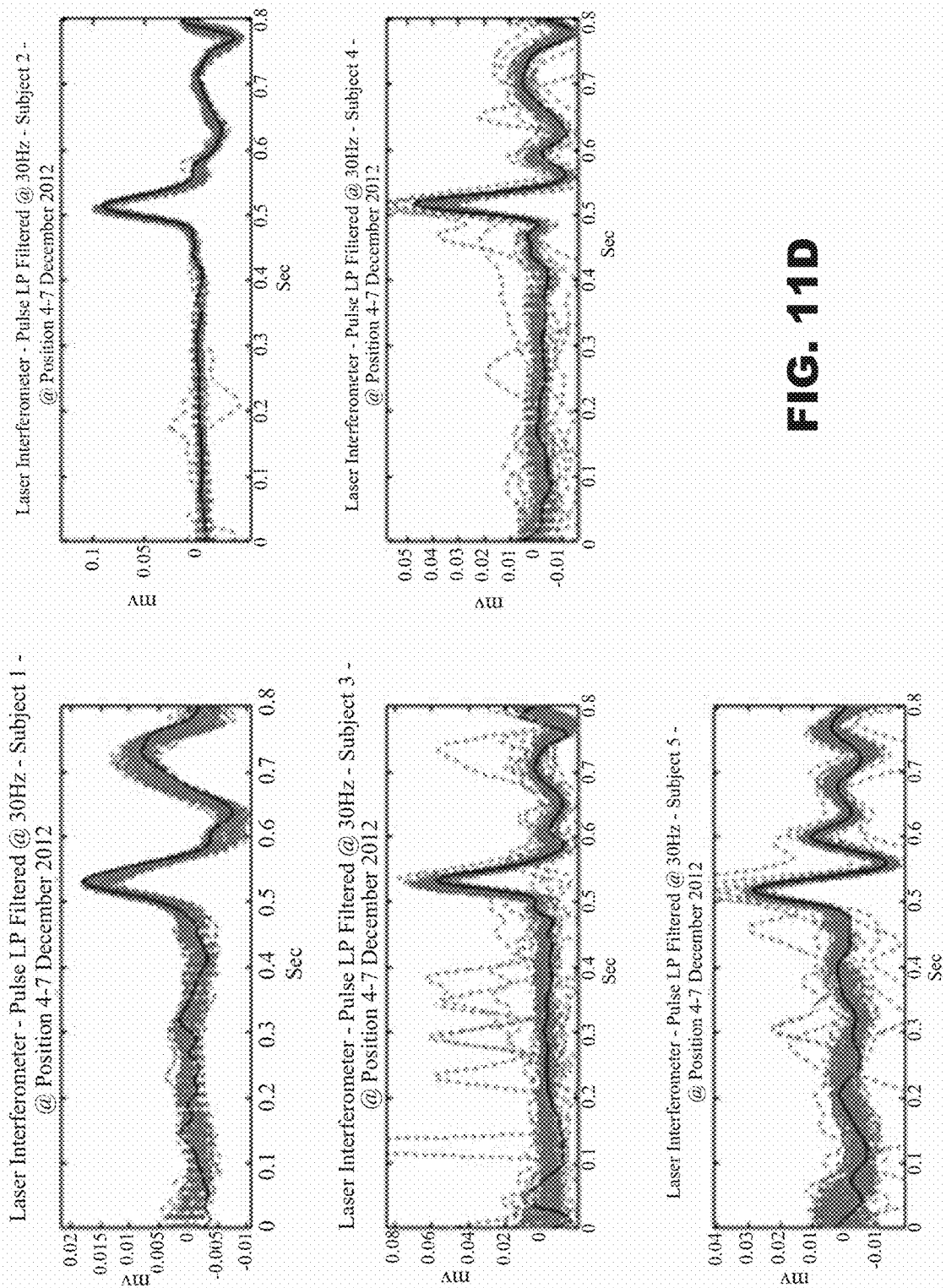
Figure 11E:
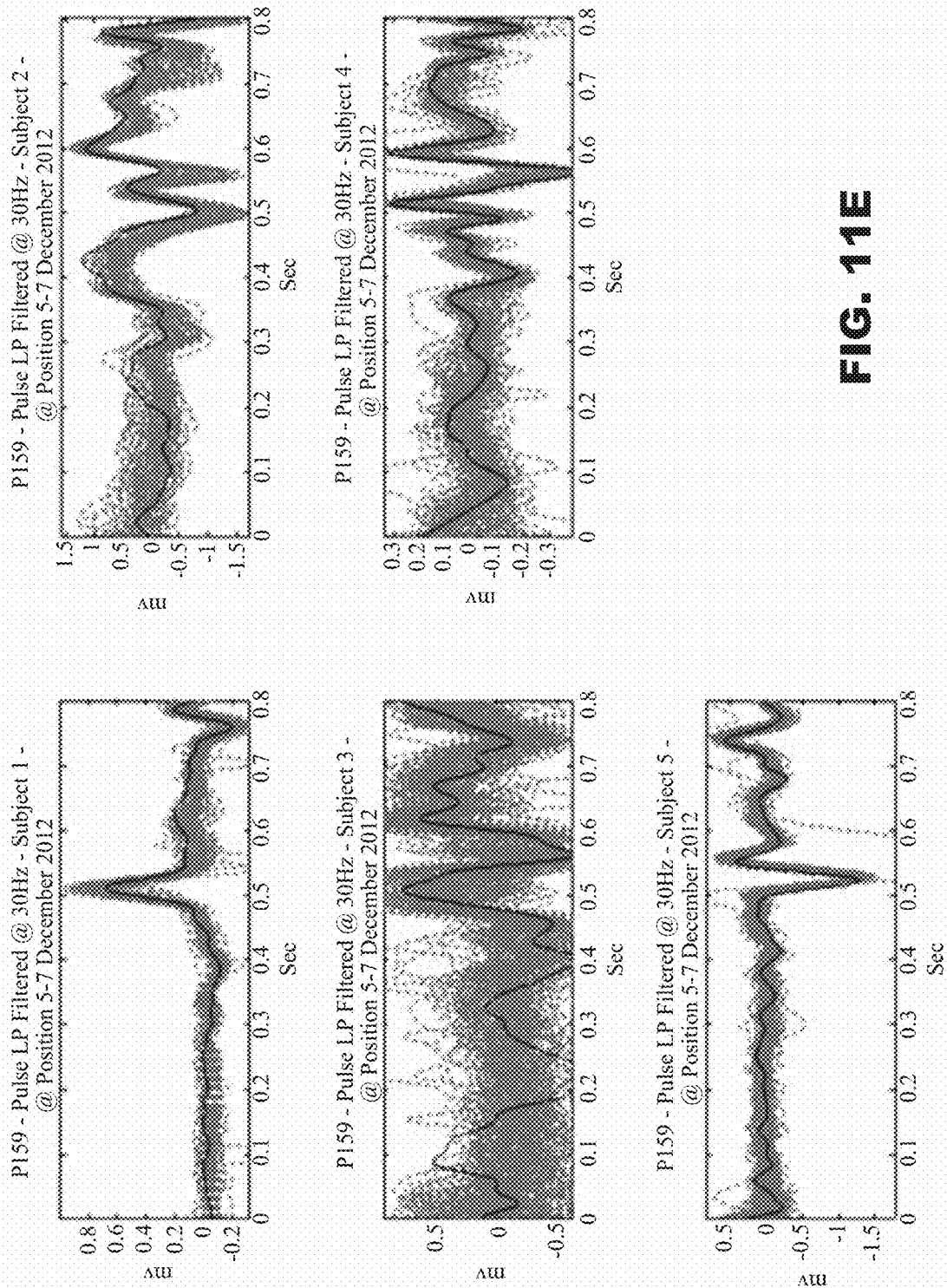

There are, however, some other positions on the neck with respect to the artery where if the acoustic sensor 1004 is placed, the signals are substantially similar over multiple subjects. For example, FIG. 11C illustrates substantially similar acoustic signals 1122, 1124, 1126, 1128, and 1130 obtained by placing an acoustic sensor at a second position with respect to the artery over five different subjects. Signals obtained from the second position also contain features, for example, a positive peak 1132, as compared to signals obtained from other positions. In another embodiment, these signals may be obtained from multiple different patients or test subjects.

In an embodiment, data representing these waveforms can be stored in a database or the like. Together, they can form an orthogonal set of basis waveforms, or eigenwaveforms, that can be used to match an individual patient's waveform with one in the set of basis waveforms (see FIG. 12). Accordingly, it may be advantageous to obtain a large sample set, for example, of acoustic pulse measurements from hundreds or thousands of patients.

VII. Probe-Off Detection Using Pulse Matching

The pulse shape vectors or template signals described with respect to FIG. 11 or other pulse shape template signals can be used to identify probe-off conditions. In one embodiment, the pulse shape vectors are stored in the patient monitor. These stored pulse shapes can be correlated with an acoustic pulse signal received from a patient. The patient may be someone whose pulse shape was not previously measured and does not have one or more pulse shape vectors stored in the set of pulse shape vectors. In another embodiment, the patient may be from the same group of subjects used to obtain a set of recorded pulse shapes. In yet another embodiment, one or more of the patient's own pulse shape previously measured and stored may be used for determining whether the sensor is properly attached to the patient. In some embodiments, the acoustic pulse signals may go through one or more low pass filters (described above) before morphology detection described with respect to FIGS. 12A-C, and 13.

Any of the probe-off detection processes described below or elsewhere herein can be used together by the probe-off detector 334. The probe-off detector 334 can arbitrate between the output of the processes or algorithms so as to output an overall probe-off detection decision. For example, each process described herein can compute a confidence value that represents the process's confidence in its probe-off (or on) determination. The probe-off detector 334 can thus execute the processes in parallel (at least in part) and evaluate their results based on the computed confidences (or execute the processes serially and then afterwards evaluate them together). The probe-off detector 334 can also apply greater weight to some of the processes than others, so as to emphasize the output of such processes over others. The probe-off detector 334 can further adapt the weights applied to each process over time based on confidence. Moreover, in other embodiments, the probe-off detector 334 combines the output of the processes to come up with an overall score or indication that represents whether or not the probe is on or off.

Figure 12A:
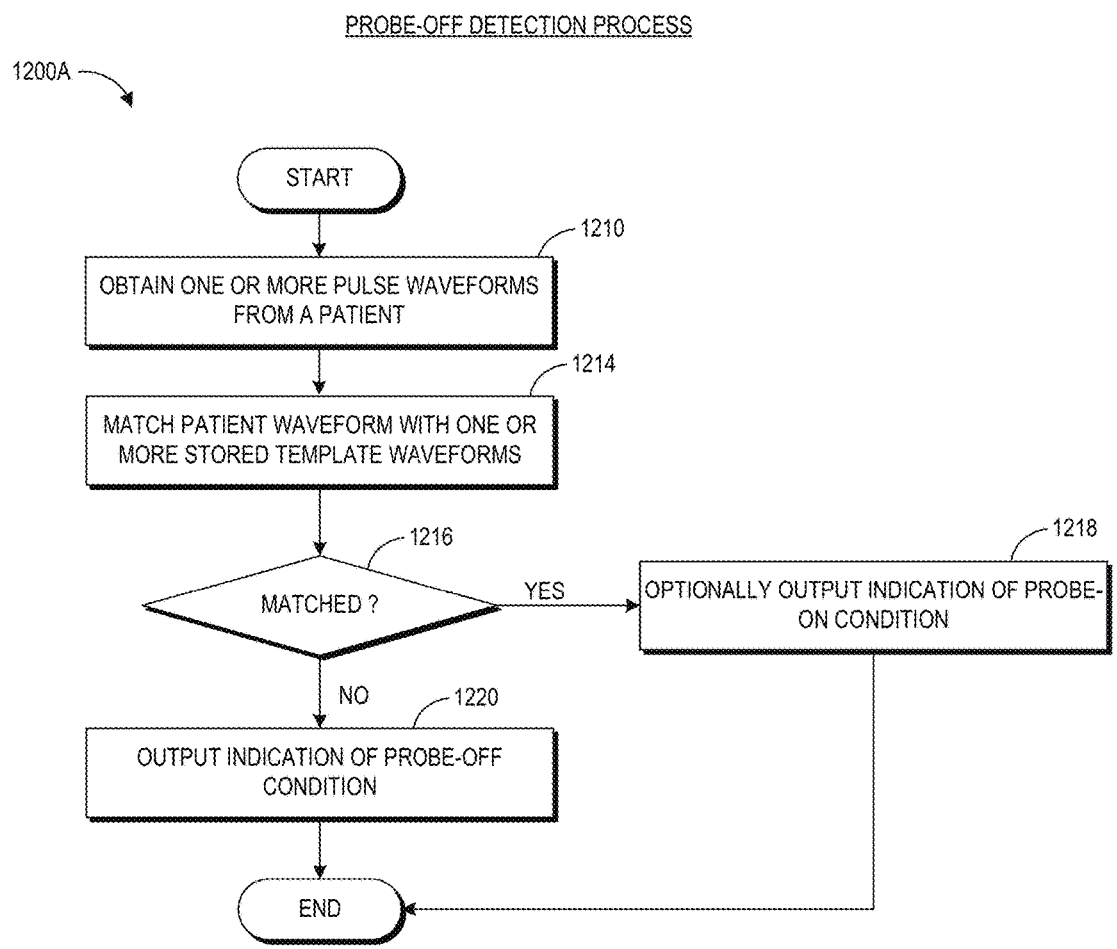
FIGS. 12A-B depict example algorithms for identifying the probe-off condition.

FIG. 12A illustrates an embodiment of a process 1200 that can determine whether the sensor is properly attached to a patient using pulse matching. The process 1200 can be implemented by any of the systems described herein, such as any of the probe-off detectors described herein.

At block 1210, one or more pulse shape waveforms may be measured from the patient using an acoustic sensor. The probe-off detector can perform pulse matching at block 1214 between the patient's pulse waveform and the set of pulse waveforms obtained and stored as described above. In one embodiment, the probe-off detector implements a matched filter to compare the patient's pulse waveform with the plurality of waveforms in the stored waveform data (collected from and/or extrapolated from other patients). In another embodiment, the probe-off detector performs the matching by first performing a wavelet transform or the like of the patient's pulse waveform using one or more of the stored waveforms. The wavelet transform can use the stored waveforms as a set of basis functions or wavelets (e.g., a Hilbert basis), which can be compared with the patient's pulse waveform to determine a degree to which the patient's waveform matches any of the stored waveforms. Thus, the output of the wavelet transform may include wavelet spectral-domain content that is indicative of which pulses the patient's waveform matches. For example, if the patient's pulse wave matches one of the stored waveforms, the wavelet transform output corresponding to that stored waveform may have a value that indicates a match between the patient's waveform and the stored waveform. The match may be less than a perfect match (e.g., due to noise) while still indicating that the patient's waveform likely corresponds to other physiologically-possible waveforms in the waveform storage. In other embodiments, the probe-off detector can use similar techniques in place of wavelet techniques using other transforms, such as the Short Time Fourier Transform, the Chirplet transform, or the Gabor transform, combinations of the same, or the like.

Viewed another way, pulse matching can be obtained by correlating a known or template signal, the set of pulse vectors, with the received acoustic signal to detect the presence of the pulse shape in the acoustic signal. This correlation can be an n-dimensional correlation (n being an integer) depending on the number of pulse shape vectors in the set. In another embodiment, pulse matching may be obtained from cross-correlation of the received acoustic signal with one or more of the set of pulse vectors. In one embodiment, the signals are not matched if the area under the cross-correlated signal is below a threshold value.

If the patient's pulse waveform matches any of the waveforms in the set of waveforms, then in an optional step at block 1218, an output indication of successful connection condition is sent. In the alternative, if the two signals are not matched, then an output indication of a probe-off condition is sent at block 1220.

Figure 12B:
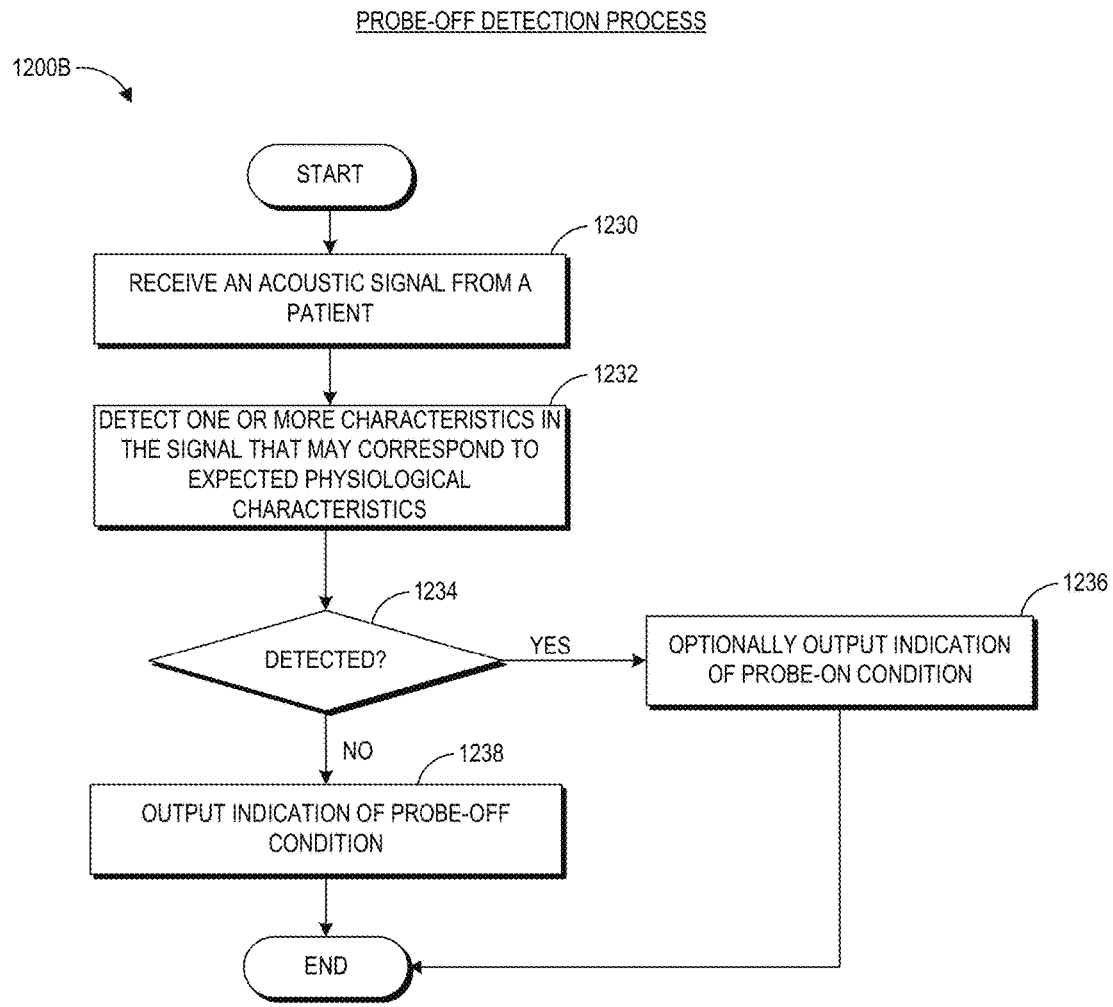

FIG. 12B illustrates an embodiment of a process 1200B that can determine whether the sensor is properly attached to a patient by detecting one or more physiological characteristics in the pulse waveforms based on the acoustic signals received from an acoustic sensor coupled to a patient. The process 1200B can be implemented by any of the systems described herein, such as any of the probe-off detectors described herein.

Acoustic signals that correspond to respiration, pulse rate, or other physiological phenomenon may be distinguished from noise by recognizing that the human body constraints such acoustic signals to certain boundary conditions. For example, while an acoustic sensor can pick up an acoustic signal from skin vibration, skin vibration may be confined to physical boundary conditions imposed by the elasticity of the skin and surrounding tissue connected to the skin. These physical boundary conditions can impose limits on the characteristics (such as amplitude) of an acoustic signal that corresponds to respiration or pulse rate. Noise signals may have greater amplitudes than respiratory and pulse rate signals, particularly if the noise is due to a sensor that is not properly attached to the patient. Thus, acoustic signal amplitude and other signal characteristics may be evaluated by a hardware processor to distinguish respiratory rate and pulse rate signals from noise, which can facilitate probe-off detection.

At block 1230, an acoustic signal can be received from a patient using an acoustic sensor attached to the neck, chest, or elsewhere on the body. The acoustic signal may be low-pass filtered to focus on potential pulse waveform data residing at low frequencies as described above. At block 1232, the probe-off detector 334 can detect one or more characteristics in the received signal that may correspond to expected physiological characteristics. For instance, the probe-off detector 334 can detect whether the amplitude of the acoustic signal exceeds a predetermined limit. The predetermined limit can correspond to observed and/or theoretical maximum skin displacement (which may be patient-dependent and corrected for baseline shift).

The probe-off detector 334 can also determine physiological characteristics from the shape of the acoustic signal. For example, the probe-off detector 334 can look for a characteristic (such as a small dip) in the pulse wavefrom that may match a dichrotic notch typically found in a photoplethysmograph waveform. The dichrotic notch is an example characteristic indicative of an actual physiological pulse signal instead of noise. Thus, if the probe-off detector 334 detects a dichrotic notch, the probe-off detector 334 can determine that the acoustic sensor 310 is attached to the patient. The probe-off detector 334 can also detect other characteristics in the pulse to evaluate a potential probe-off condition. Other characteristics may include features corresponding to the heart sounds, and in particular, the second heart sound (S2), inflection points, peaks, and dips. In one embodiment, when the first characteristic is detected corresponding to a physiological feature in a pulse waveform, the probe-off detector can look for a second characteristic in the pulse waveform following the first characteristic. The second characteristic may be based on a stored waveform shapes and/or physiological phenomenon. Accordingly, in some embodiments, the detection can include looking for two or more features in the pulse waveform in particular order.

In some embodiments, the probe-off detector 334 can check for one or more other characteristics described above and output a confidence measurement based on the number of characteristics detected. Thus, based on the detecting one or more characteristics, in an optional step at block 1236, an output indication of a successful connection condition can be sent, indicating that the sensor is properly placed on the patient. In the alternative, if no characteristics are detected or if the signal does not have physical characteristics other than noise, then an output indication of a probe-off condition is sent at block 1238.

Figure 13:
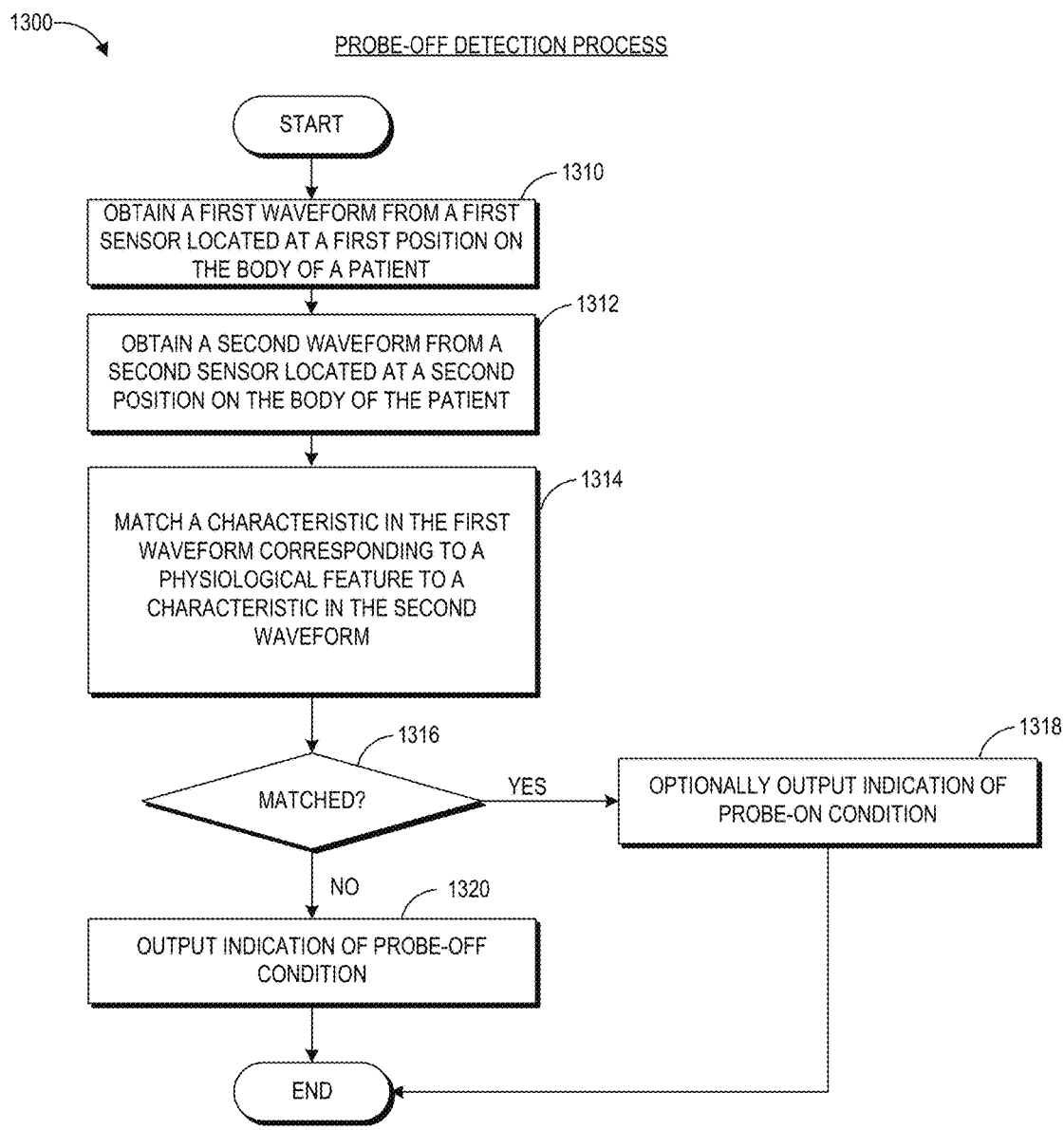
FIG. 13 depicts an example algorithm for identifying the probe-off condition.

FIG. 13 illustrates an embodiment of a process 1300 that can determine whether the sensor is properly attached to a patient by matching one or more characteristics in the pulses received from acoustic sensors positioned at different parts of a patient's body. The process 1300 can be implemented by any of the systems described herein, such as any of the probe-off detectors described herein. At block 1310, a first acoustic waveform from a first sensor located at a first position on the body of a patient may be obtained by a patient monitor. At block, 1312, a second acoustic waveform from a second sensor located at a second position on the body of the patient may be obtained by the patient monitor.

The first acoustic waveform from the first acoustic sensor may include different physiological features compared to the second acoustic waveform from a second acoustic sensor depending on the placement of each of the acoustic sensors on body of a patient. The first acoustic signal may also share some features with the second acoustic signal depending on receiving some shared physiological characteristics. Accordingly, the first and the second acoustic signals may have some shared and some different morphologies. In addition, the first and the second acoustic signal may be orthogonal because they are collected from different parts of the body. As an example, the first acoustic sensor can be placed near a carotid artery at the neck of a patient and the second acoustic sensor can be placed on the chest near the heart of the patient. The second acoustic signal received near the chest may include features corresponding to both the first and second heart sounds (S1 and S2), while the first acoustic signal near the carotid artery at the neck may include a feature corresponding to the second heart sound (S2) but not the first (S1). The probe-off detector 334 can correlate the two acoustic signals to determine whether both signals include the S2 sound. If so, the probe-off detector 334 can determine that one or both of the acoustic sensors is properly placed on the patient.

Accordingly, at step 1314, if the characteristic is found in both acoustic signals, the probe-off detector 334 can optionally output an indication of successful a connection. If the characteristic is not found in both signals, then an output indication of a probe-off condition is sent at block 1260.

VIII. Example User Interface

Figure 14A:
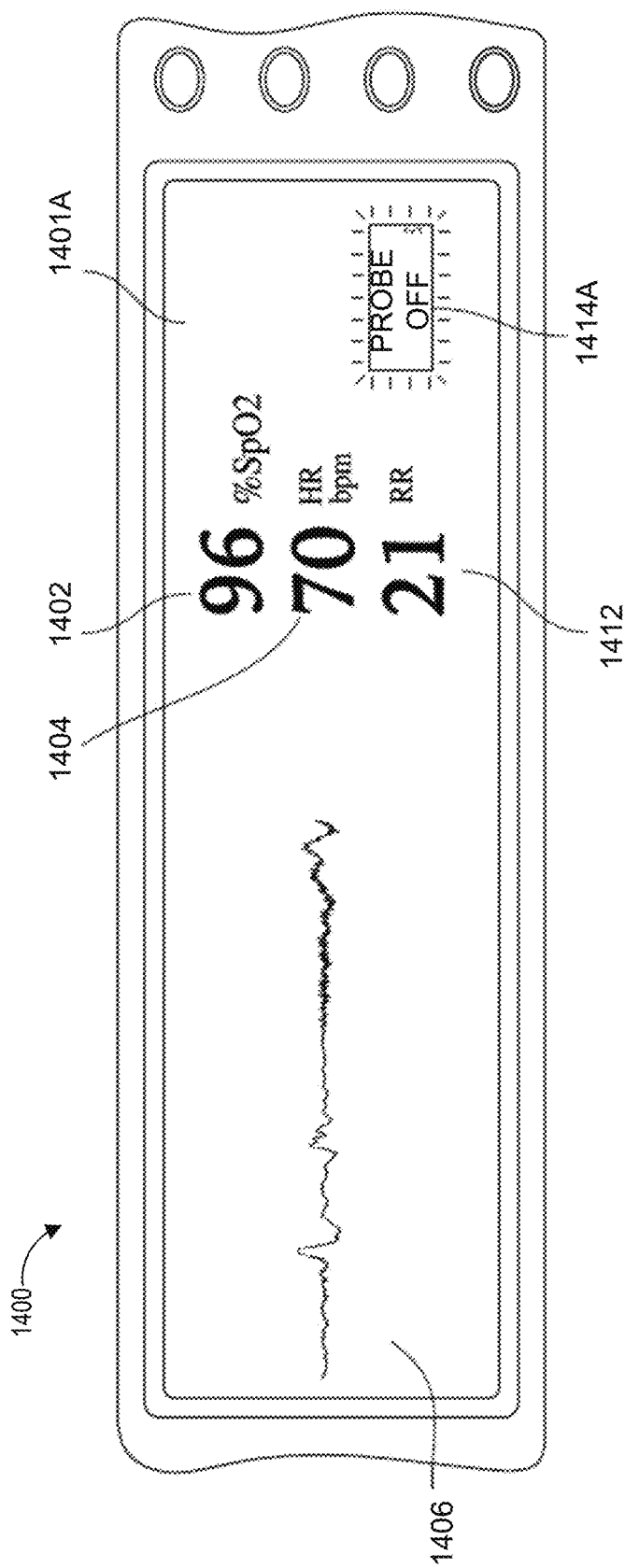
FIGS. 14A-B illustrate example multiparameter physiological monitor displays.
Figure 14B:
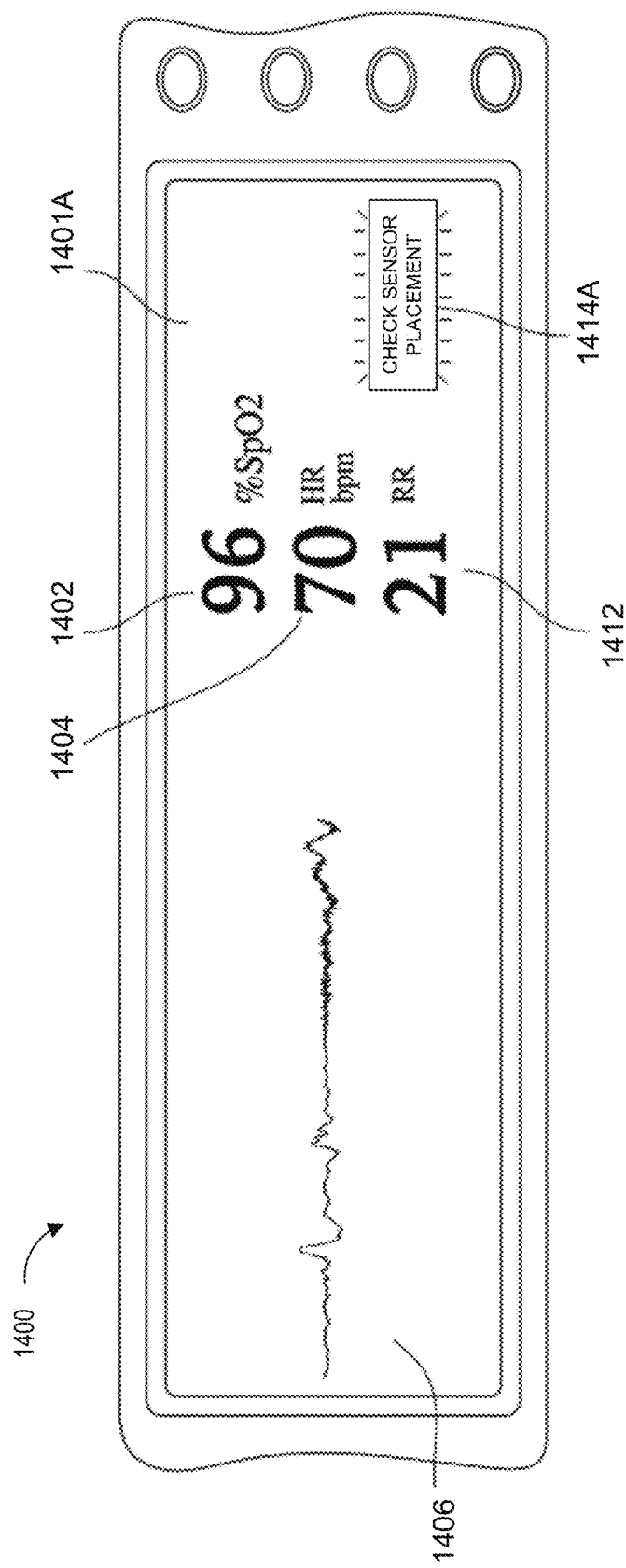

FIGS. 14A-B illustrate example multiparameter physiological monitor displays 1400. The display 1401*a* can output a probe-off indicator 1414*a*. The probe-off indicator 1414*a* can be generated using any of the techniques described above. The example display 1400 shown includes parameter data for respiratory rate, including a measured respiratory rate value 1412 in breaths per minute (bpm) and an acoustic physiological signal 1406. The probe-off indicator 1414*a* can separately indicate the connection quality of the attached acoustic sensor. The display 1401A also includes parameter data for SpO2 1402, and pulse rate 1404 in beats per minute (BPM). In the depicted embodiment shown in FIG. 14A, the probe-off indicator 1414A includes text that indicates that the sensor is not properly attached to the patient. In some embodiments, the probe-off indicator 1114A includes text indicating that the sensor placement needs to checked, as shown in FIG. 14B. The text displayed in the probe-off indicator 114 may depend on a confidence calculation from one of the probe-off detection processes described above. Each one of the probe-off processes described above may have different confidence rating depending on how accurately the particular process or combination of processes can predict a probe-off condition. The confidence rating may be stored in the patient monitor. In some embodiments, more than one of probe-off processes (described above) can be used to determine the probe-off indicator 1114A.

IX. Additional Embodiments

Each of the algorithms for detecting a probe-off condition described above, although described separately, can work together to refine a probe-off detector. For instance, some or all of the techniques described herein may operate in parallel (and/or in series) to produce a decision from each algorithm. The patient monitor can implement decision logic to decide whether to output a probe-off indication or alarm based on the outputs of the various algorithms. Each algorithm may also output a confidence score that indicates a degree to which the algorithm is confident that its result is accurate. The confidence score may be in any suitable range, such as [0, 1] or some other range. The decision logic can use the confidence scores to determine whether to output a probe-off indicator. Further, confidence scores or indicators can be output by an individual algorithm that is not being used in a parallel fashion.

As an example, the probe-off detector may determine 1) whether energy in the low frequency spectrum exceeds a threshold, 2) whether pulse rate calculated from an acoustic sensor and from an optical sensor are within a threshold range, and 3) whether the pulse waveform of the patient matches any pulse waveforms in a dataset of waveform data, as described above. The probe-off detector can assign a confidence score based on the results of each algorithm. A decision logic module of the probe-off detector can then evaluate, based on these scores and outputs, whether to output an indication of a probe-off condition. In an embodiment, if the majority of the algorithms indicated that probe-off likely occurred, the decision logic can output a probe-off indication. In another embodiment, if fewer than a majority of the algorithms output a probe-off indication but the confidence scores of these algorithms exceeds a threshold, the decision logic may output a probe-off indication. Many other embodiments and configurations of the decision logic are possible.

In certain embodiments, a method of determining a connection state between a non-invasive acoustic sensor and a medical patient can include receiving an acoustic physiological signal from an acoustic sensor coupled with a medical patient. In some embodiments, the method can further include receiving a second physiological signal from a second sensor coupled with the medical patient. The method can also include the step of comparing, with one or more processors, the acoustic physiological signal and the second physiological signal. In some embodiments, the method can include step of, in response to said comparison, outputting an indication of whether one or both of the non-invasive acoustic sensor and the second sensor is properly connected to the patient.

The method of preceding paragraph, wherein the step of outputting an indication can include text indicating that a sensor connection needs to be checked.

In some embodiments, a method of determining a connection state between a non-invasive acoustic sensor and a medical patient can include receiving an acoustic physiological signal from an acoustic sensor coupled with a medical patient. The method can further include the step of extracting a low frequency waveform from the acoustic physiological signal. In some embodiments, the method can include the step of detecting one or more characteristics in the low frequency waveforms that correspond to predetermined physiological features and in response to detecting that the low frequency waveform does not have any characteristics, outputting a probe-off indication. In an alternate embodiment, the method can include the step of detecting a first feature in the low frequency waveform that corresponds to a first physiological feature and detecting a second feature in the waveform that corresponds to a second physiological feature in time. In response to detecting the second feature, the method can include the step of outputting an indication whether the sensor is properly connected to the patient.

In some embodiments, a method of determining a connection state between a non-invasive acoustic sensor and a medical patient can include receiving a first acoustic physiological signal from a first acoustic sensor coupled with a medical patient and receiving a second acoustic physiological signal from a second acoustic sensor coupled with the medical patient at different location than the first acoustic sensor. The method can further include the step of extracting a low frequency waveforms from the first and the second acoustic physiological signals. In some embodiments, the method can include the step of matching a characteristic in the first acoustic physiological signal to a characteristic in the second acoustic physiological signal. In response to matching, the method can include the step of outputting an indication whether the sensor is properly connected to the patient.

X. Terminology

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method of determining a connection state between a non-invasive acoustic sensor and a medical patient, the method comprising:
   receiving an acoustic physiological signal from an acoustic sensor configured to couple with a medical patient;
   receiving a photoplethysmograph (PPG) waveform from an optical sensor configured to couple with the medical patient;
   extracting low frequency components from the acoustic physiological signal;
   extracting high frequency components from the acoustic physiological signal;
   calculating an acoustic pulse rate measurement from the extracted low frequency components;
   calculating a respiration rate measurement from the extracted high frequency components;
   calculating an optical pulse rate measurement from the PPG waveform;
   determining a difference between the acoustic pulse rate measurement calculated from the acoustic physiological signal and the optical pulse rate measurement calculated from the PPG waveform;
   comparing the difference with a threshold value; and
   in response to said comparison, outputting the calculated respiration rate measurement with an indication of connection quality of the non-invasive acoustic sensor.

2. The method of claim 1, wherein the low frequency components are extracted by a low pass filter.

3. The method of claim 1, wherein the high frequency components are extracted using a pass band filter.

4. A system for determining a connection state between a non-invasive acoustic sensor and a medical patient, the system comprising:
   one or more processors configured to:
      receive an acoustic physiological signal from an acoustic sensor configured to couple with a medical patient;
      receive a photoplethysmograph (PPG) waveform from an optical sensor configured to couple with the medical patient;
      extract low frequency components from the acoustic physiological signal;
      extract high frequency components from the acoustic physiological signal;
      calculate an acoustic pulse rate measurement from the extracted low frequency components;
      calculate a respiration rate measurement from the extracted high frequency components;
      calculate an optical pulse rate measurement from the PPG waveform;
      determine, with one or more processors, a difference between the acoustic pulse rate measurement and the optical pulse rate measurement;
      compare the difference with a threshold value; and
      output the respiration rate measurement with an indication of connection state of the acoustic sensor based on the comparison.

5. The system of claim 4, wherein the low frequency components are extracted by a low pass filter.

6. The system of claim 5, wherein the high frequency components are extracted by a passband filter.

7. A method of determining a connection state between a non-invasive acoustic sensor and a medical patient, the method comprising:
   receiving an acoustic physiological signal from an acoustic sensor, the acoustic physiological signal reflecting first physiological information of a patient;
   receiving a photoplethysmograph ("PPG") waveform from an optical sensor, the PPG signal reflecting second physiological information of the patient;
   extracting a first feature from the acoustic physiological signal corresponding to a physiological feature;
   extracting a second feature from the PPG waveform corresponding to the same physiological feature;
   extracting high frequency components from the acoustic physiological signal;
   calculating a respiration rate measurement from the high frequency components of the acoustic physiological signal;

comparing, with one or more processors, an acoustic pulse rate measure from the acoustic physiological signal and the optical pulse rate measure from PPG signal;

determining an indication of connection state of the acoustic sensor in response to said comparing the acoustic pulse rate measure with the optical pulse rate measure; and outputting the respiration rate measurement with the indication of connection state of the acoustic sensor.

8. The method of claim 7, wherein said comparing comprises computing a cross-correlation between a portion of the acoustic physiological signal and the PPG signal.

* * * * *